United States Patent
Kim et al.

(10) Patent No.: US 10,710,951 B2
(45) Date of Patent: *Jul. 14, 2020

(54) PHARMACEUTICAL COMPOSITION CONTAINING VERBENONE DERIVATIVE FOR TREATING OR PREVENTING NEURODEGENERATIVE DISEASE

(71) Applicant: KOREA UNIVERSITY RESEARCH AND BUSINESS FOUNDATION, Seoul (KR)

(72) Inventors: Won Ki Kim, Seoul (KR); Yongseok Choi, Gyeonggi-do (KR); Sumi Song, Gyeonggi-do (KR)

(73) Assignee: SHIN POONG PHARMACEUTICAL CO., LTD., Gyeonggi-Do (KR)

( * ) Notice: Subject to any disclaimer, the term of this patent is extended or adjusted under 35 U.S.C. 154(b) by 308 days.

This patent is subject to a terminal disclaimer.

(21) Appl. No.: 15/432,522

(22) Filed: Feb. 14, 2017

(65) Prior Publication Data

US 2017/0166505 A1   Jun. 15, 2017

Related U.S. Application Data

(63) Continuation of application No. 14/405,152, filed as application No. PCT/KR2013/004932 on Jun. 4, 2013, now Pat. No. 9,603,842.

(30) Foreign Application Priority Data

Jun. 5, 2012   (KR) .................. 10-2012-0060314

(51) Int. Cl.
*A61K 31/4402*   (2006.01)
*A61K 31/402*   (2006.01)
(Continued)

(52) U.S. Cl.
CPC ............ *C07C 49/86* (2013.01); *A23L 29/055* (2016.08); *A23L 33/105* (2016.08);
(Continued)

(58) Field of Classification Search
None
See application file for complete search history.

(56) References Cited

U.S. PATENT DOCUMENTS

| 5,223,542 A | 6/1993 | Byers et al. |
| 6,214,888 B1 | 4/2001 | Ren et al. |

(Continued)

FOREIGN PATENT DOCUMENTS

| WO | 9306823 A1 | 4/1993 |
| WO | 0063159 A1 | 10/2000 |
| WO | WO0168576 A1 | 9/2001 |

OTHER PUBLICATIONS

Belayev, L., et al., "Middle cerebral artery occlusion in the rat by intraluminal suture. Neurological and pathological evaluation of an improved model.", "Stroke", Sep. 1996, pp. 1616-1623, vol. 27, No. 9.

(Continued)

*Primary Examiner* — Savitha M Rao
*Assistant Examiner* — Andrew P Lee
(74) *Attorney, Agent, or Firm* — Hultquist, PLLC; Steven J. Hultquist

(57) ABSTRACT

The present invention relates to a pharmaceutical composition or a functional health food comprising a verbenone derivative and pharmaceutically acceptable salts thereof as active ingredients for treating or preventing a neurodegenerative disease. More specifically, the verbenone derivative according to the present invention reduces neuronal cell death and oxidative stress, and is highly effective in preventing ischemic brain damage and inflammatory cell (Continued)

8 Claims, 10 Drawing Sheets
(6 of 10 Drawing Sheet(s) Filed in Color)

(51) Int. Cl.
    *A61K 31/122* (2006.01)
    *C07C 49/86* (2006.01)
    *A61K 31/401* (2006.01)
    *A23L 29/00* (2016.01)
    *A23L 33/105* (2016.01)
    *A61K 45/06* (2006.01)
    *A61K 31/18* (2006.01)
    *A61K 31/4406* (2006.01)
    *A61K 31/4409* (2006.01)
    *A61K 31/045* (2006.01)
    *A61K 31/435* (2006.01)
    *A61K 31/495* (2006.01)
    *A61K 31/53* (2006.01)
    *C07C 49/798* (2006.01)
    *C07C 49/813* (2006.01)
    *C07C 49/835* (2006.01)
    *C07D 207/02* (2006.01)
    *C07D 213/50* (2006.01)

(52) U.S. Cl.
CPC .......... *A61K 31/045* (2013.01); *A61K 31/122* (2013.01); *A61K 31/18* (2013.01); *A61K 31/401* (2013.01); *A61K 31/402* (2013.01); *A61K 31/435* (2013.01); *A61K 31/4402* (2013.01); *A61K 31/4406* (2013.01); *A61K 31/4409* (2013.01); *A61K 31/495* (2013.01); *A61K 31/53* (2013.01); *A61K 45/06* (2013.01); *C07C 49/798* (2013.01); *C07C 49/813* (2013.01); *C07C 49/835* (2013.01); *C07D 207/02* (2013.01); *C07D 213/50* (2013.01); *A23V 2002/00* (2013.01); *C07C 2602/42* (2017.05)

(56) References Cited

U.S. PATENT DOCUMENTS

| | | |
|---|---|---|
| 6,649,658 B1 | 11/2003 | Corvi Mora et al. |
| 2015/0148362 A1 | 5/2015 | Kim et al. |

OTHER PUBLICATIONS

Bernardes, W., et al., "Antibacterial activity of the essential oil from Rosmarinus officinalis and its major components against oral pathogens", "Z. Naturfosch C.", Sep.-Oct. 2010, pp. 588-593, vol. 65.

Chaturvedi, S. "Acetylsalicylic acid + extended-release dipyridamole combination therapy for secondary stroke prevention", "Clin. Ther.", Jul. 2008, pp. 1196-1205, vol. 30, No. 7.

Choi, Y., et al., "Methyleugenol reduces cerebral ischemic injury by suppression of oxidative injury and inflammation", "Free Radical Research", Aug. 2010, pp. 925-935, vol. 44, No. 8.

Choi, I., et al., "Anti-ischemic and anti-inflammatory activity of (S)-cis-verbenol", "Free Radical Research", May 2010, pp. 541-551, vol. 44, No. 5.

Choi, I., et al., "A3 adenosine receptor agonist reduces brain ischemic injury and inhibits inflammatory cell migration in rats", "The American Journal of Pathology", Aug. 18, 2011, pp. 2042-2052, vol. 179, No. 4.

Choi, I. et al., "Activation of cannabinoid CB2 receptor-mediated AMPK/CREB pathway reduces cerebral ischemic injury", "The American Journal of Pathology", Feb. 13, 2013, pp. 928-939, vol. 182, No. 3.

Colbourne, F. et al., "Continuing postischemic neuronal death in CA1: influence of ischemia duration and cytoprotective doses of NBQX and SNX-111 in rats", "Stroke", Mar. 1999, pp. 662-668, vol. 30, No. 3.

Culmsee, C., et al., "Combination therapy in ischemic stroke: synergistic neuroprotective effects of memantine and clenbuterol", "Stroke", Apr. 1, 2004, pp. 1197-1202, vol. 35, No. 5.

Danziger, D.J., et al., "Automated site-directed drug design: a general algorithm for knowledge acquisition about hydrogen-bonding regions at protein surfaces", "Proceedings of the Royal Society of London", Mar. 22, 1989, pp. 101-113, vol. 236 B.

Dirngal, U., et al, "Pathobiology of ischaemic stroke: an integrated view", "Trends Neurosci", Sep. 1999, pp. 391-397, vol. 22, No. 9.

Firuzi, O., et al., "Antioxidant Therapy: Current Status and Future Prospects", "Current Medicinal Chemistry", Sep. 2011, pp. 3871-3888, vol. 18, No. 25.

Halperin, I., et al., "Biomarkers for Evaluation of Clinical Efficacy of Multipotential Neuroprotective Drugs for Alzheimers and Parkinsons Diseases", "Neurotherapeutics", Jan. 2009, pp. 128-140, vol. 6, No. 1.

Hatfield, R., et al, "The dose-response relationship and therapeutic window for dizocilpine (MK-801) in a rat focal ischaemia model", "European Journal of Pharmacology", May 27, 1992, pp. 1-7, vol. 216, No. 1.

Huang, D., et al., "The Chemistry behind Antioxidant Capacity Assays", "Journal of Agricultural and Food chemistry", Mar. 23, 2005, pp. 1841-1856, vol. 53, No. 6.

Jin, D., et al., "Anti-oxidant and anti-inflammatory activities of macelignan in murine hippocampal cell line and primary culture of rat microglial cells", "Biochemical and Biophysical Research Communications", Jun. 17, 2005, pp. 1264-1269, vol. 331, No. 4.

Ju, C., et al., "Up-regulation of astroglial heme oxygenase-1 by a synthetic (S)-verbenone derivative LMT-335 ameliorates oxygenglucose deprivation-evoked injury in cortical neurons", "Biochemical and Biophysical Research communications", Jan. 16, 2013, pp. 484-489, vol. 431, No. 3.

Kang, G., et al., "Neuroprotective effect of fucoidin on lipopolysaccharide accelerated cerebral ischemic injury through inhibition of cytokine expression and neutrophil infiltration", "Journal of the Neurological Sciences", May 2, 2012, pp. 25-30, vol. 318.

Lee, J., et al., "Accelerated Cerebral Ischemic Injury by Activated Macrophages/Microglia After Lipopolysaccharide Microinjection into Rat Corpus Callosum", "Glia", Apr. 15, 2005, pp. 168-181, vol. 50, No. 2.

Lim, C., et al., "Antioxidant and anti-inflammatory activities of the methanolic extract of Neorhodomela aculeate in hippocampal and microglial cells", "Biol. Pharm. Bull.", Jun. 2006, pp. 1212-1216, vol. 29, No. 6.

Liu, R., et al., "Combination Therapy of 17beta-Estradiol and Recombinant Tissue Plasminogen Activator for Experimental Ischemic Stroke", "The Journal of Pharmacology and Experimental Therapeutics", Dec. 1, 2009, pp. 1006-1012, vol. 332, No. 3.

Margall, I. et al, "Short therapeutic window for MK-801 in transient focal cerebral ischemia in normotensive rats", "Journal of Cerebral Blood Flow and Metabolism", Jan. 1996, pp. 107-113, vol. 16, No. 1.

Martinez-Velazquez, M., et al., "Acaricidal effect of essential oils from Lippia graveolens (Lamiales: Verbenaceae), Rosmarinus officinalis (Lamiales: Lamiaceae), and Allium sativum (Liliales: Liliaceae) against Rhipicephalus (Boophilus) microplus (Acari: Ixodidae)", "Journal of Medical Entomology", Jul. 2011, pp. 822-827, vol. 48, No. 4.

Nguyen, T., et al., "A novel reactivity of SeO2 with 1,3-dienes: Formation of syn 1,2- and 1,4-diols via a facile C—Se bond oxidation", "Organic Letters", Oct. 4, 2001, pp. 3161-3163, vol. 3, No. 20.

Nguyen, T., et al., "Novel Reactivity of SeO2 with 1,3-Dienes: Selenophene Formation", "J. Org. Chem.", Sep. 6, 2002, pp. 6553-6556, vol. 67, No. 18.

(56) References Cited

OTHER PUBLICATIONS

Price, C., et al., "Human cellular inflammation in the pathology of acute cerebral ischaemia", "J Neurol Neurosurg Psychiatry", Nov. 2003, pp. 1476-1484, vol. 74, No. 11.

Rodrigo, R., et al., "Oxidative Stress and Pathophysiology of Ischemic Stroke: Novel Therapeutic Opportunities", "CNS & Neurological Disorders—Drug Targets", Aug. 2013, pp. 698-714, vol. 12.

Salama, M., et al, "Co-Enzyme Q10 to Treat Neurological Disorders: Basic Mechanisms, Clinical Outcomes, and Future Research Direction", "CNS & Neurological Disorders—Drug Targets", Aug. 2013, pp. 641-664, vol. 12, No. 5.

Sonkusare, S., et al., "Dementia of Alzheimer's disease and other neurodegenerative disordersmemantine, a new hope", "Pharmacological Research", Jan. 2005, pp. 1-17, vol. 51.

Standridge, J., "Pharmacotherapeutic Approaches to the Treatment of Alzheimer's Disease", "Clinical Therapeutics", May 2004, pp. 615-630, vol. 26, No. 5.

Stanzione, P., et al., "Drugs and clinical trials in neurodegenerative diseases", "Ann Ist Super Sanita", Jan. 2011, pp. 49-54, vol. 47.

Swanson, R., et al., "A semiautomated method for measuring brain infarct volume", "Journal of Cerebral Blood Flow and Metabolism", Mar. 1990, pp. 290-293, vol. 10, No. 2.

Valtysson, J., et al, "Neuropathological endpoints in experimental stroke pharmacotherapy: the importance of both early and late evaluation", "Acta Neurochir (Wien)", 1994, pp. 58-63, vol. 129.

Von Lubitz, D., et al., "MK-801 is neuroprotective but does not improve survival in severe forebrain ischemia", "European Journal of Pharmacology", Mar. 16, 1993, pp. 95-100, vol. 233.

Yang, Y., et al., "Quantification of infarct size on focal cerebral ischemia model of rats using a simple and economical method", "Journal of Neuroscience Methods", Oct. 1, 1998, pp. 9-16, vol. 84.

Yoshida, H., et al, "Neuroprotective Effects of Edaravone: a Novel Free Radical Scavenger in Cerebrovascular Injury", "CNS Drug Reviews", 2006, pp. 9-20, vol. 12, No. 1.

Note: For the non-patient literature citations that no month of publication is indicated, the year of publication is more than 1 year prior to the effective filing date of the present application.

Kaufmann, D., et al., "Myrtenal Inhibits Acetylcholinesterase, a Known Alzheimer Target", "Journal of Pharmacy nd Pharmacology", 2011, pp. 1368-1371, vol. 63.

PHARMACEUTICAL COMPOSITION CONTAINING VERBENONE DERIVATIVE FOR TREATING OR PREVENTING NEURODEGENERATIVE DISEASE

CROSS-REFERENCE TO RELATED APPLICATIONS

This is a continuation under 35 U.S.C. § 120 of U.S. patent application Ser. No. 14/405,152 filed Dec. 2, 2014 for PHARMACEUTICAL COMPOSITION CONTAINING VERBENONE DERIVATIVE FOR TREATING OR PREVENTING NEURODEGENERATIVE DISEASE, which in turn is a U.S. national phase under the provisions of 35 U.S.C. § 371 of International Patent Application No. PCT/KR2013/004932 filed Jun. 4, 2013, which in turn claims priority of Korean Patent Application No. 10-2012-0060314 filed Jun. 5, 2012. The disclosures of all such patent applications are hereby incorporated herein by reference in their respective entireties, for all purposes.

TECHNICAL FIELD

The present invention relates to the novel use of a verbenone derivative for treating a degenerative brain disease, and more particularly to a pharmaceutical composition for preventing or treating a degenerative brain disease, which contains a verbenone derivative or a salt thereof, which has effects on the inhibition of excitotoxicity-induced neuronal death, the inhibition of oxidative stress, and the inhibition of the migration or infiltration of intravascular inflammatory cells (e.g., macrophages and neutrophils) into an injured brain area, and to a method of preventing or treating a degenerative brain diseases using the composition.

BACKGROUND ART

Degenerative brain diseases are age-related diseases caused by the dysfunction of neurons, and social interest in degenerative brain diseases has increased with a rapid increase in the aging population. Degenerative brain diseases are classified according to major clinical symptoms and affected brain areas, and include Alzheimer's disease, Parkinson's disease, Huntington's disease, multiple sclerosis and amyotrophic lateral sclerosis.

Degenerative brain diseases are known to be caused by the death of neurons that are most important in the transmission of information in the cerebral nervous system, defects in the formation or functions of synapses that transmit& information among neurons, and abnormalities or decreases in the electrical activity of neurons, but these are still difficult to be radically treated, and the causes thereof are also still unclear.

With the recent development of cell and molecular biology, the causes of degenerative brain diseases and the development of therapeutic agents against degenerative brain diseases have been actively investigated. Studies on the development of therapeutic agents against degenerative brain diseases have been focused mainly on the following: (1) stimulation of cholinergic activity; (2) antagonism against NMDA (N-methyl-D-aspartate) receptors; (3) molecular and cell biological studies on the metabolism of (3-amyloid or Tau protein, and the development of vaccine and therapeutic antibodies against (3-amyloid-generating protein as an antigen; (4) induction of the expression of neurotrophic factor; (5) development of antioxidants capable of inhibiting causative protein-induced oxidative damage to neuronal cells; and (6) development of anti-inflammatory drugs capable of inhibiting inflammatory responses caused by the excessive infiltration and activity of inflammatory cells (Sonkusare et al., Pharmacological Research, 51(1), 1-17, 2005; Stanaione et al., Ann 1st Super Sanita, 47(1), 49-54, 2011; Halperin et al., Neurotherapeutics, 6(1), 128-140, 2009).

An AChE inhibitor, that is a cholinergic agent, inhibits the degradation of ACh and thus restores the activity of cholinergic neurotransmitters. As such AChE inhibitors, tarcrien, donepezil, rivastigmine and galanthamine were approved by the FDA, and are currently on the market.

It was reported that oxidative stress is an important cause of degenerative brain diseases of the central nervous system, such as Alzheimer's disease, Parkinson's disease, and Huntington's disease (Jin D Q et al, Biochemical and Biophysical Research Communications, 331, 1264-1269, 2005; Lim C S et al, Biological and Pharmaceutical Bulletin, 29, 1212-1216, 2006).

The number of patients with ischemic vascular diseases (myocardiac infarction, stroke, and thrombosis) in the world was 25 million in 2007, and is expected to continue to increase to 28 million in 2017 (DataMonitor, 2007). In most of OECD countries, ischemic vascular diseases were the first leading cause of death (226.6 persons per 100,000 persons in the year 2004), followed by cancer (165.6 persons). Stroke is divided into hemorrhagic stroke characterized by brain tissue injury caused by disruption of brain blood vessels, and ischemic stroke that is brain infarction caused by blockage of the flow of blood into the brain. Stroke is a disease with a very high incidence, which is the first or second leading cause of death along with cancer in every year in Korea (the 2002 to 2008 data by the Korea National Statistical Office), and Korea ranks the second of OECD countries in terms of the rate of death caused by stroke. According to the 2008 report of the American Heart Association (AHA), 65.5 billion dollars are expended annually for stroke to treat and to care ischemic vascular diseases, but the size of the therapeutic agent market for stroke is only 1.3 billion dollars. Thus, active efforts have been made to develop therapeutic agents for ischemic stroke that will have a potential market size of 22 or more billion dollars if any therapeutic agents with proven efficacy are put on the market in a few years.

In Korea, stroke is the first leading cause of death, and ranks higher than those in highly developed countries, including the USA, Canada, Australia and the like. Stroke destroys the quality of life by causing damage to motor and sensory functions, and abnormalities in higher-order functions such as memory, learning, operation and deduction, and causes much mental and physical pains to patients and their family until patients die. In recent years, as the aging population has increased rapidly, the incidence of stroke and an increase in survival time after the onset of stroke becomes a big social problem. Thus, it is required to develop therapeutic drugs for alleviating the symptoms and treating stroke.

Despite the clinical significance of stroke and the big market size as mentioned above, the development of therapeutic agents for stroke is still insignificant, and clinically approved therapeutic agents for stroke include only tissue plasminogen activator (t-PA). Stroke is caused by various reasons, and comprises various diseases with different etiologic factors including brain infarction, cerebral hemorrhage and subarachnoid hemorrhage and the like. In addition, stroke may be caused by various cerebrovascular diseases, including arteriosclerosis, cerebral amyloid angiopathy, and aortic dissection, and may also be caused by cardiogenic embolism due to arrhythmia or coronary artery disease. The causes of stroke are diverse as described above, but in terms of cell biology, it is considered that a decrease in blood supply and the resulted cell death are the common mechanism. For this reason, the understanding of mechanism for ischemic neuronal cell death is a core technology to develop the therapeutic strategies for stroke prevention, control, and treatment.

In Korea and other countries, many research groups have made efforts to prevent brain diseases by studying the mechanism of neuronal death as mentioned above. In the case of stroke, a distinctive therapeutic agent has not yet been developed, and many clinical doctors are reluctant to use even t-PA, the sole therapeutic agent that is clinically used to dissolve thrombi produced in brain blood vessels, because of its side effects such as cerebral hemorrhage. Until now, many research groups have attempted to develop a therapeutic agent for stroke based on either an antagonist against glutamic acid receptor that is an excitatory neurotransmitter, or an antioxidant, but such attempts have failed due to insignificant efficacy or toxicity of drugs.

The time taken for a stroke patient to reach a hospital emergency room after the onset of stroke is usually several hours or more. Within several minutes to several hours after the onset of stroke, neuronal cells are primarily damaged by excitatory neurotoxicity caused by the excessive release of glutamic acid, and are secondarily damaged by exposure to the excessive oxygen and nitrogen radicals produced with the passage of time. After a few tens of hours, the neuronal cells are continuously and severely damaged by inflammatory responses, and in this case, it is clinically meaningless to use an excitatory neurotoxicity inhibitor.

As mentioned above, stroke is not a disease caused by a single factor, but is a disease that causes brain injury by various pathways and mechanisms of cell death. In recent years, there have been attempts to obtain a synergistic therapeutic effect against stroke by the use of drugs with different mechanisms in combination. For example, the administration of aspirin in combination with dipyridamole showed a favorable prognosis for stroke compared to the administration of aspirin alone (Chatuvedi S., Clin Therap, 30(7), 1196-205, 2008). In addition, a combination of 17O-estradiol and tPA extended the therapeutic time window in ischemic stroke patients, because 17O-estradiol reduced cerebral hemorrhage caused by increased expression of urokinase, MMP2 and MMP9 caused by tPA (Liu R. et al., J Pharmacol Exp Ther, 332(3), 1006-12, 2010). The administration of Memantine (that is an NMDA receptor antagonist) in combination with Clenbuterol (that is beta-adrenalin beta 2 receptor agonist) showed a synergistic effect on the inhibition of ischemic brain injury in a permanent focal ischemic model. Also, the administration of memantine in combination with the calcium ion blocker Topiramate showed a synergistic effect on the inhibition of hypoxia-induced brain injury in neonatal rats (Culmsee C. et al., Stroke, 35(5), 1197-202, 2004). However, such studies are mostly intended to alleviate symptoms, and did not show synergistic effects based on protective mechanisms for brain tissue.

In order to understand ischemic brain tissue injury caused by ischemia and develop a drug for inhibiting this brain tissue injury, the mechanism and pathway of brain tissue injury after ischemia should be understood. Generally, brain cell injury or death after ischemia is caused by various factors. For example, it is known that excitotoxicity, peri-infract depolarization, oxidative stress, and inflammation are associated with the development of ischemic brain injury (Dirnagl et al., Trends Neurosci., 22, 391-397, 1999). Thus, it is crucial to understand the very diverse temporal profiles (e.g., onset and duration) and to properly interrupt their pathopathological cascades.

Neuronal death by excitotoxicity can be inhibited by a glutamate receptor antagonist, and ionic receptors on which glutamate acts are AMPA ($\alpha$-amino-3-hydroxy-5-methyl-4-iso-xazolepropionic acid), kainate, and NMDA (N-methyl-D-aspartate) receptors. Particularly, many studies on cell death by NMDA receptor activity have been conducted (Standridge J. B., Clin. Ther., 26(5), 615-630, 2004). However, despite such efforts, the NMDA receptor blockers were not successful in clinical trials, because they had insignificant effects or were toxic. The NMDA receptor blocker MK-801 significantly reduced ischemic brain injury, but had a great disadvantage of a brief therapeutic time window. MK-801 showed a neuron protection effect in rats and gerbils only when it was administered within 1 hour after onset of focal ischemia (Margaill et al., J Cereb Blood Flow Metab, 16, 107-113, 1996; Hatfield R H et al., Eur J Pharmacol, 216, 1-7, 1992). Also, MK-801 delays postischemic neuronal death, but does not improve either neurological recovery or endpoint survival after several weeks of treatment (Valtysson J. et al., Acta Neurochir (Wien), 129, 58-63, 1994; Von Lubitz D K et al., Eur J Pharmacol, 233, 95-100, 1993). Receptors of the excitatory neurotransmitter glutamic acid include AMPA receptor together with NMDA receptor. Antagonists for the AMPA receptors did not show significant protective effects against neurological deficit at 28 days after MCAO (Colbourne F et al., Stroke, 30, 662-668, 1999). The short therapeutic window and lack of long-term therapeutic effect of NMDA or AMPA receptor antagonists suggest that such receptors perform only a transient role in the early ischemic cascade. Thus, other pathophysiological processes that are not affected by these treatments are thought to contribute to the delayed cerebral ischemic damage.

As various degenerative diseases, oxidative stress has a very great effect on the death or loss of function of cells in stroke. Thus, studies on the therapeutic effects of antioxidants for ischemic stroke have been actively conducted (Salama M. et al., Co-Enzyme Q10 to Treat Neurological Disorders: Basic Mechanisms, Clinical Outcomes, and Future Research Direction. CNS Neurol Disord Drug Targets. 2013; Rodrigo R. et al., Oxidative Stress and Pathophysiology of Ischemic Stroke: Novel Therapeutic Opportunities. CNS Neurol Disord Drug Targets. 2013). In Japan, Edaravone having antioxidant effect as its major mechanism is put on the market as a therapeutic agent for stroke (Firuzi O et al., Curr Med Chem., 18(25), 3871-88, 2011; Yoshida H. et al., CNS Drug Rev., 12(1), 9-20. 2006).

Several hours after excitatory neurotoxicity after ischemia, an inflammatory response is initiated in the injured brain area, and continued for several days to several weeks to worsen brain injury. Thus, in recent years, attempts to treat ischemic stroke using anti-inflammatory agents have been actively made (Price C J et al., J Neurol Neurosurg Psychiatry, 74, 1476-1484, 2003; Salama M, Co-Enzyme Q10 to Treat Neurological Disorders: Basic Mechanisms, Clinical Outcomes, and Future Research Direction. CNS Neurol Disord Drug Targets. 2013; Rodrigo R. et al., Oxidative Stress and Pathophysiology of Ischemic Stroke: Novel Therapeutic Opportunities. CNS Neurol Disord Drug Targets. 2013). Also, it was recently reported that inflammatory cells infiltrated from blood vessels plays a major role in the aggravation of brain injury in ischemic stroke (Kang G H et al., J Neurol Sci., 15, 318(1-2), 25-30, 2012; Choi I Y et al., Am J Pathol., 179(4), 2042-52, 2012; Choi Y K et al., Free Radic Res., 44(8), 925-35, 2010; Choi I Y et al., Free Radic Res., 44(5), 541-51, 2010; Lee J C et al., Glia, 50(2), 168-81, 2005). In addition, it was reported that anti-inflammatory responses mediated by cannabinoid B2 receptor inhibit damage to ischemic brain tissue (Choi I Y et al., Am J Pathol, 182(3), 928-39, 2013).

Thus, it is considered that the development of drugs having various cell protection activities is essential for complete treatment of stroke. To achieve this purpose, that is, to develop a pleiotrophic therapeutic drug having various cell protection mechanisms, the present inventors have developed a derivative of (1S)-(−)-verbenone. (1S)-(−)-verbenone is a natural anti-aggregation pheromone generated by bark beetles from a host tree resin precursor, alpha-pinene. Essential oils containing (1S)-(−)-verbenone have been reported to exhibit biological activities such as anti-microbial activity or insecticidal activity (Bernarde W A, Z Naturforsch C, 65, 588-93, 2010; Martinez-Velazquez M., J Med Entomol, 48, 822-827, 2011). In addition, WO 2000/63159 discloses that verbenone[(1S, 5S)-4,6,6-trimethylbicyclo[3.3.3] hept-3-en-2one) and its derivatives have anti-inflammatory effects in the airway.

However, the above patent document neither discloses nor suggests the effects of verbenone derivatives on the reduction of neuronal death and oxidative stress, the inhibition of ischemic brain injury and the inhibition of migration of inflammatory cells.

Accordingly, the present inventors have measured NMDA-induced excitotoxicity and cell death in a hypoxic-ischemic rat model in order to examine the effects of verbenone derivatives on the reduction of neuronal death and oxidative stress and the inhibition of ischemic brain injury and inflammatory responses, and performed an experiment on the antioxidant activities of verbenone derivatives. As a result, the present inventors have first found that verbenone derivatives have an effect on the treatment of degenerative brain diseases. More specifically, the present inventors have found that verbenone derivatives according to the present invention reduce neuronal death and oxidative stress, and exhibit excellent effects on the inhibition of ischemic brain injury and inflammatory responses in vivo, thereby completing the present invention.

DISCLOSURE OF INVENTION

The object of the present invention is to provide the novel use of a verbenone derivative for preventing or treating a degenerative brain disease.

To achieve the above object, the present invention provides a pharmaceutical composition for preventing or treating a degenerative brain disease, the composition comprising, as an active ingredient, a verbenone derivative having a structure of Formula 1 or a pharmaceutically acceptable salt thereof:

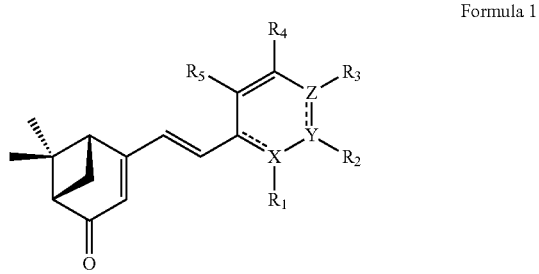

Formula 1 wherein $R_1$, $R_2$, $R_3$, $R_4$ and $R_5$ are each independently at least one selected from a hydrogen atom, a halogen atom selected from among F, Cl, Br and I, a hydroxyl group, a $C_1$-$C_3$ alkyl group, a $C_1$-$C_3$ alkoxy group, an amino group, a $C_1$-$C_3$ alkylamine group, a $C_1$-$C_3$ alkyldiamine group, a $C_5$-$C_8$ aromatic ring, a $C_5$-$C_8$ cyclic ring, and a $C_5$-$C_8$ heteroaromatic ring; X, Y and Z are each independently a carbon atom or at least one heteroatom selected from the group consisting of N, O and S atoms; and denotes a double bond or a single bond.

In the present invention, the mentioned verbenone derivative may function to reduce neuronal death and oxidative stress, inhibit ischemic brain injury, and inhibit the migration of inflammatory cells.

In the present invention, the degenerative brain disease may be stroke, palsy, dementia, Alzheimer's disease, Parkinson's disease, or Huntington's disease. Specifically, it may be stroke, vascular dementia, or dementia of Alzheimer type. More specifically, it may be stroke, and even more specifically ischemic stroke disease.

In the present invention, the composition may further contain a suitable carrier, excipient or diluent that is generally used in the preparation of pharmaceutical compositions.

In the present invention, the composition may be formulated or used in combination with one or more drugs selected from the group consisting of calcium channel blockers, antioxidants, glutamate antagonists, anticoagulants, antihypertensive drugs, antithrombotic drugs, antihistamines, anti-inflammatory drugs, anticancer drugs, and antibiotics.

The present invention also provides the use of a verbenone derivative having a structure of Formula 1 or a pharmaceutically acceptable salt thereof for preventing or treating a degenerative brain disease.

The present invention also provides a method of preventing or treating a degenerative brain disease using a verbenone derivative having a structure of Formula 1 or a pharmaceutically acceptable salt thereof.

The present invention also provides a method for preventing or treating a degenerative brain disease, the method comprising administering to a subject a verbenone derivative having a structure of Formula 1 or a pharmaceutically acceptable salt thereof.

The present invention also provides a functional food for preventing or alleviating a degenerative brain disease, the food comprising, as an active ingredient, a verbenone derivative having a structure of Formula 1.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Figure 1:
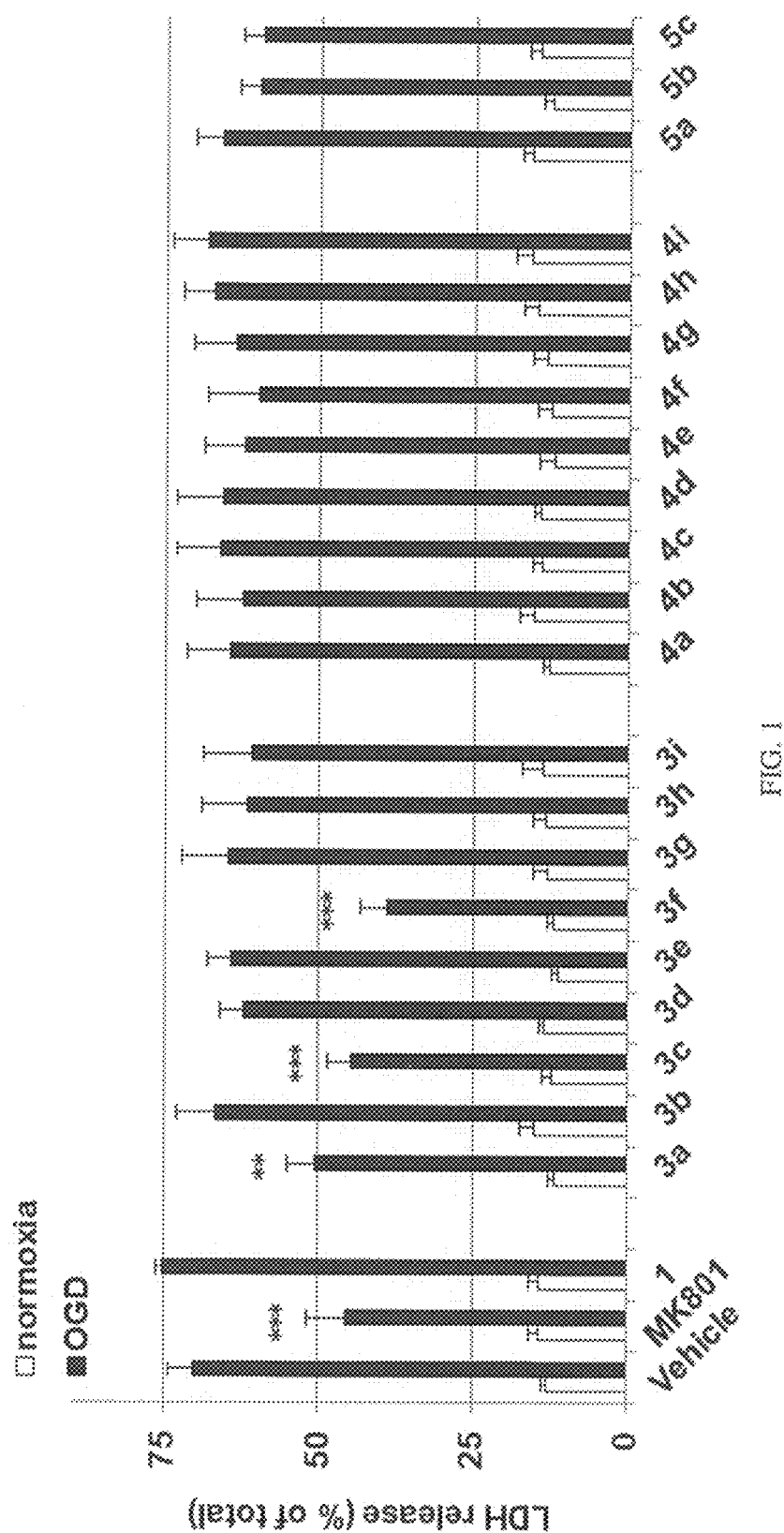
FIG. 1 shows the effects of compound derivatives of the present invention on the protection of rat cortical neuronal cells.

In one aspect, the present invention is directed to the novel use of a verbenone derivative having a structure of Formula 1:

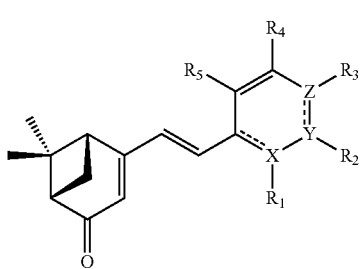

Formula 1 wherein $R_1$, $R_2$, $R_3$, $R_4$ and $R_5$ are each independently at least one selected from a hydrogen atom, a halogen atom selected from among F, Cl, Br and I, a hydroxyl group, a $C_1$-$C_3$ alkyl group, a $C_1$-$C_3$ alkoxy group, an amino group, a $C_1$-$C_3$ alkylamine group, a $C_1$-$C_3$ alkyldiamine group, a $C_5$-$C_8$ aromatic ring, a $C_5$-$C_8$ cyclic ring, and a $C_5$-$C_8$ heteroaromatic ring; X, Y and Z are each independently a carbon atom or at least one heteroatom selected from the group consisting of N, O and S atoms; and denotes a double bond or a single bond.

Among compounds belonging to the definition of Formula I, preferred are compounds wherein $R_1$, $R_2$, $R_3$, $R_4$ and $R_5$ are each independently at least one selected from the group consisting of a hydrogen atom, a halogen atom selected from among F, Cl, Br and I, a hydroxyl group, a methyl group, an ethyl group, a methoxy group, an ethoxy group, an amino group, a $C_5$-$C_6$ aromatic ring, a $C_5$-$C_6$ cyclic ring, and a $C_5$-$C_6$ heteroaromatic ring, and more preferably at least one selected from a hydrogen, a halogen atom selected from among F, Cl, Br and I, a hydroxyl group, a methyl group, a methoxy group, a phenyl group, a pyrrole group, and a pyridine group; and X, Y and Z are each independently a carbon atom or at least one heteroatom selected from the group consisting of N, O and S atoms, and more preferably at least one atom selected from the group consisting of a carbon atom and an N atom.

The most preferable compound of the group of compounds belonging to the definition of Formula I is selected from the following compounds:

(1S,5R)-4-(4-hydroxystyryl)-6,6-dimethylbicyclo[3.1.1]hept-3-en-2-one (3a);
(1S,5R)-4-(4-hydroxy-2-methoxystyryl)-6,6-dimethylbicyclo[3.1.1]hept-3-en-2-one (3b);
(1S,5R)-4-(3,4-dihydroxystyryl)-6,6-dimethylbicyclo[3.1.1]hept-3-en-2-one (3c);
(1S,5R)-4-(3-Bromo-4-hydroxystyryl)-6,6-dimethylbicyclo[3.1.1]hept-3-en-2-one (3d);
(1S,5R)-4-(4-hydroxy-2,6-dimethoxystyryl)-6,6-dimethylbicyclo[3.1.1]hept-3-en-2-one (3e);
(1S,5R)-4-(3,4-dihydroxy-5-methoxystyryl)-6,6-dimethylbicyclo[3.1.1]hept-3-en-2-one (3f);
(1S,5R)-4-(3-hydroxystyryl)-6,6-dimethylbicyclo[3.1.1]hept-3-en-2-one (3g);
(1S,5R)-4-(2-hydroxystyryl)-6,6-dimethylbicyclo[3.1.1]hept-3-en-2-one (3h);
(1S,5R)-4-(2-hydroxy-4-methoxystyryl)-6,6-dimethylbicyclo[3.1.1]hept-3-en-2-one (3i);
(1S,5R)-6,6-dimethyl-4-styryl-bicyclo[3.1.1]hept-3-en-2-one (4a);
(1S,5R)-4-(4-fluorostyryl)-6,6-dimethylbicyclo[3.1.1]hept-3-en-2-one (4b);
(1S,5R)-4-(4-methoxystyryl)-6,6-dimethylbicyclo[3.1.1]hept-3-en-2-one (4c);
(1S,5R)-4-(2-(biphenyl-4-yl)vinyl)-6,6-dimethylbicyclo[3.1.1]hept-3-en-2-one (4d);
(1S,5R)-4-(4-(1H-pyrrol-1-yl)styryl)-6,6-dimethylbicyclo[3.1.1]hept-3-en-2-one (4e);
(1S,5R)-4-(3,4-dimethoxystyryl)-6,6-dimethylbicyclo[3.1.1]hept-3-en-2-one (4f);
(1S,5R)-4-(3,5-dimethoxystyryl)-6,6-dimethylbicyclo[3.1.1]hept-3-en-2-one (4g);
(1S,5R)-4-(2,5-dimethoxystyryl)-6,6-dimethylbicyclo[3.1.1]hept-3-en-2-one (4h);
(1S,5R)-4-(5-bromo-2-methoxystyryl)-6,6-dimethylbicyclo[3.1.1]hept-3-en-2-one (4i);
(1S,5R)-6,6-dimethyl-4-(E)-2-(pyridin-2-yl)vinyl)-bicyclo[3.1.1]hept-3-en-2-one (5a);
(1S,5R)-6,6-dimethyl-4-(E)-2-(pyridin-3-yl)vinyl)-bicyclo[3.1.1]hept-3-en-2-one (5b); and
(1S,5R)-6,6-dimethyl-4-(E)-2-(pyridin-4-yl)-vinyl)-bicyclo[3.1.1]hept-3-en-2-one (5c).

The inventive compounds represented by Formula 1 may be prepared as pharmaceutically acceptable salts or solvates according to conventional methods known in the art.

A pharmaceutically acceptable salt is preferably an acid addition salt formed with a pharmaceutically acceptable free acid. An acid addition salt may be prepared using a conventional, for example, by dissolving a compound in an excess amount of aqueous acid solution to form a salt and precipitating the formed salt using a water-miscible organic solvent, such as methanol, ethanol, acetone or acetonitrile. Alternatively, an acid addition salt may be formed by heating an equimolar amount of a compound and an acid in water or alcohol (e.g., glycol monomethyl ether), and then drying the mixture by evaporation or filtering the precipitated salt by suction.

Herein, the free acid may be an inorganic acid or an organic acid. Examples of the inorganic acids include hydrochloric acid, phosphoric acid, sulfuric acid, nitric acid and stannic acid, and examples of the organic acids include methanesulfonic acid, p-toluenesulfonic acid, acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbic acid, carbonic acid, vanillic acid, and hydroiodic acid.

In addition, a pharmaceutically acceptable metal salt may be prepared using a base. An alkali metal or alkaline earth metal salt may be obtained, for example, by dissolving a compound in an excess amount of alkali metal hydroxide or alkaline earth metal hydroxide solution, filtering undissolved salt, and then drying the filtrate by evaporation. As the metal salts, sodium, potassium or calcium salts are pharmaceutically suitable. Also, the corresponding silver salts may be obtained by reacting an alkali metal or alkaline earth metal salt with a proper silver salt (e.g., silver nitrate).

Unless otherwise indicated herein, pharmaceutically acceptable salts of the compounds having a structure of Formula 1 include salts of acidic or basic groups, which may be present in the compounds of Formula 1. For example, the pharmaceutically acceptable salts include sodium, calcium and potassium salts of a hydroxyl group, and other pharmaceutically acceptable salts of an amino group, including hydrobromide, sulfate, hydrogen sulfate, phosphate, hydrogen phosphate, dihydrogen phosphate, acetate, succinate, citrate, tartrate, lactate, mandelate, methanesulfonate (mesylate) and para-toluenesulfonate (tosylate). The salts may be prepared using a salt preparation method known in the art.

The compounds of Formula 1 may be prepared by synthesis methods known in the art, and may be chemically synthesized by the methods shown in the following reaction schemes, but are not limited thereto.

Reaction Scheme 1

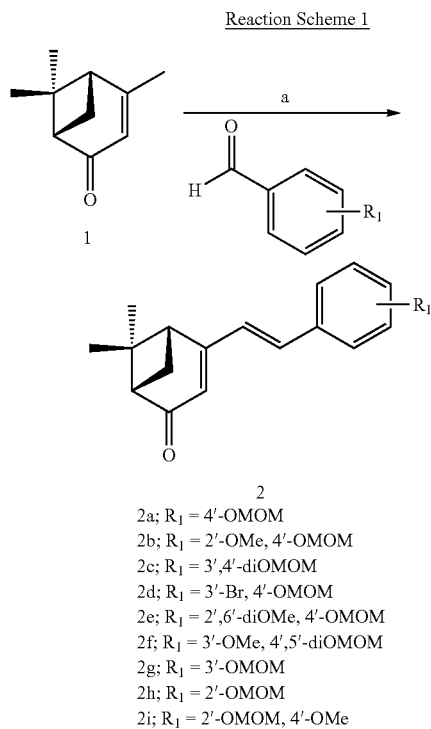

2a; $R_1$ = 4'-OMOM
2b; $R_1$ = 2'-OMe, 4'-OMOM
2c; $R_1$ = 3',4'-diOMOM
2d; $R_1$ = 3'-Br, 4'-OMOM
2e; $R_1$ = 2',6'-diOMe, 4'-OMOM
2f; $R_1$ = 3'-OMe, 4',5'-diOMOM
2g; $R_1$ = 3'-OMOM
2h; $R_1$ = 2'-OMOM
2i; $R_1$ = 2'-OMOM, 4'-OMe

-continued

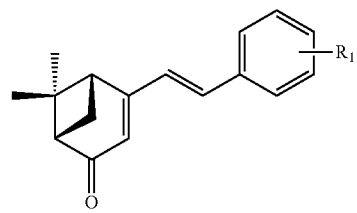

3
3a; $R_1$ = 4'-OH
3b; $R_1$ = 2'-OMe, 4'-OH
3c; $R_1$ = 3',4'-diOH
3d; $R_1$ = 3'-Br, 4'-OH
3e; $R_1$ = 2',6'-diOMe, 4'-OH
3f; $R_1$ = 3'-OMe, 4',5'-diOH
3g; $R_1$ = 3'-OH
3h; $R_1$ = 2'-OH
3i; $R_1$ = 2'-OH, 4'-OMe

ªReaction and condition: a) KOH, MeOH, 60° C., 6 h; b) 10% HCl, MeOH, rt, 24 h.

Commercially available (1S)-(−)-verbenone (1) may be condensed with benzaldehyde derivatives (2a-i) having a hydroxystyryl group in the presence of a base, and then deprotected with acid, thereby various verbenone derivatives (3a-i) having an alkoxy or bromo substituent or a phenolic functional group.

Reaction Scheme 2

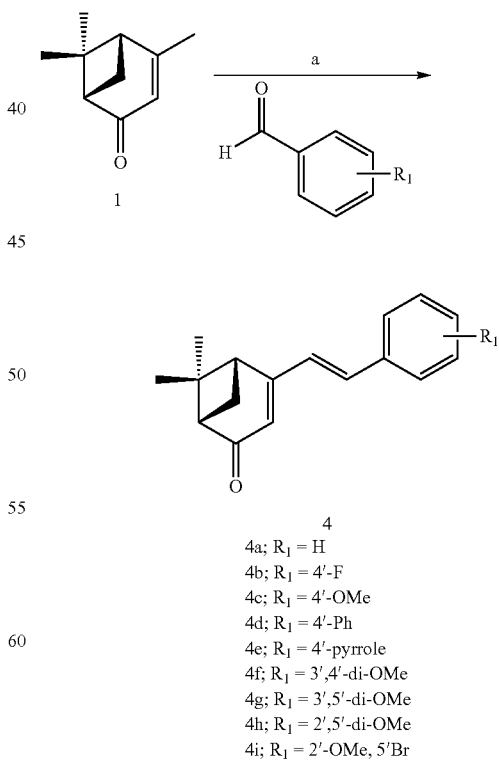

4
4a; $R_1$ = H
4b; $R_1$ = 4'-F
4c; $R_1$ = 4'-OMe
4d; $R_1$ = 4'-Ph
4e; $R_1$ = 4'-pyrrole
4f; $R_1$ = 3',4'-di-OMe
4g; $R_1$ = 3',5'-di-OMe
4h; $R_1$ = 2',5'-di-OMe
4i; $R_1$ = 2'-OMe, 5'Br ªReaction and condition: a) KOH, MeOH, 60° C., 6 h.

Reaction Scheme 3

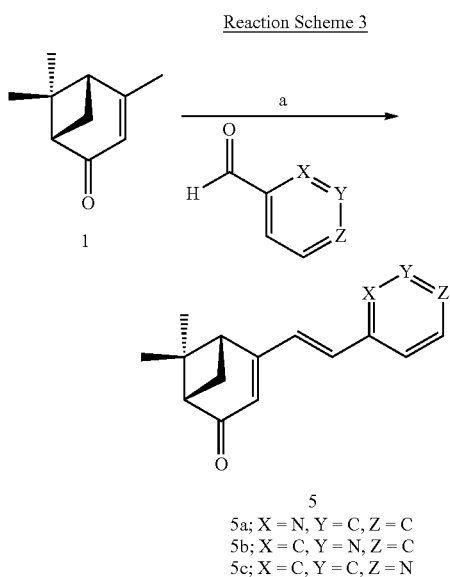

5
5a; X = N, Y = C, Z = C
5b; X = C, Y = N, Z = C
5c; X = C, Y = C, Z = N

[a]Reaction and condition: a) NaOMe, MeOH, 60° C., 6 h.

In another method for synthesizing derivatives, commercially available (1S)-(−)-verbenone (1) may be subjected to a process similar to the process of Reaction Scheme 1 so as to introduce a styryl group into derivatives having various functional groups, thereby preparing various verbenone derivatives (4a-i, 5a-c) having an aromatic ring.

In the present invention, the novel effects of verbenone derivatives on the treatment of the degenerative brain disease were analyzed. As a result, it was found that verbenone derivatives inhibited NMDA-induced excitotoxicity and intracellular oxidative stress, increased antioxidant activity, inhibited the migration and infiltration of inflammatory cells, and inhibited the expression of cytokines. The results of the analysis are described in detail in the Examples below.

In another aspect, the present invention is directed to the use of a verbenone derivative having a structure of Formula 1 or a pharmaceutically acceptable salt thereof for preventing or treating a degenerative brain disease.

In addition, the present invention is directed to a pharmaceutical composition for preventing or treating a degenerative brain disease, the composition comprising, as an active ingredient, a verbenone derivative having a structure of Formula 1 or a pharmaceutically acceptable salt thereof, and a method of preventing or treating a degenerative brain disease using a verbenone derivative having a structure of Formula 1 or a pharmaceutically acceptable salt thereof.

In an embodiment, the present invention relates to a method for preventing or treating a degenerative brain disease, the method comprising administering to a subject a verbenone derivative having a structure of Formula 1 or a pharmaceutically acceptable salt thereof. Herein, the administration may be performed in vivo or in vitro.

In the present invention, the degenerative brain disease may be selected from the group consisting of stroke, palsy, dementia, Alzheimer's disease, Parkinson's disease, Huntington's disease, multiple sclerosis and amyotrophic lateral sclerosis. As used herein, the term "degenerative brain disease" means any disease caused by the death of neurons that are most important in the transmission of information in the cerebral nervous system, defects in the formation or functions of synapses that transmit information among neurons, or abnormalities or decreases in the electrical activity of neurons.

In the present invention, the degenerative brain disease is preferably stroke, and more preferably ischemic stroke disease.

The pharmaceutical composition according to the present invention can be administered by various routes, including, but not limited to, oral, intravenous, intramuscular, intra-arterial, intramedullary, intradural, intracardial, transdermal, subcutaneous, intraperitoneal, intranasal, gastrointestinal, local, sublingual, and rectal routes. Preferably, the pharmaceutical composition of the present invention is administered orally or parenterally. As used herein, the term "partenteral" includes subcutaneous, intradermal, intravenous, intramuscular, intra-articular, intra-synovial, intrasternal, intrathecal, intralesional and intracranial injection or infusion techniques. The pharmaceutical composition of the present invention may also be administered in the form of suppositories for rectal administration.

The pharmaceutical composition of the present invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The dose level of the pharmaceutical composition of the present invention will depend upon a variety of factors, including the activity of the specific compound employed, the age, body weight, general health status, sex, diet, time of administration, route of administration, rate of excretion, drug combination, and the severity of the specific disease to be prevented or treatebhyd. The pharmaceutical composition according to the present invention can be formulated in the form of pills, sugar-coated tablets, capsules, liquid, gel, syrup, slurry or suspensions.

In the present invention, the pharmaceutical composition may be formulated or used in combination with one or more agents selected from the group consisting of calcium channel blockers, antioxidants, glutamate antagonists, anticoagulants, antihypertensives, antithrombotic agents, anti-histamine agents, anti-inflammatory agents, anticancer agents, and antibiotics.

In still another aspect, the present invention is directed to a method for preventing or treating a degenerative brain disease, the method comprising administering, to a subject, a pharmaceutical composition for preventing or treating a degenerative brain disease, the composition comprising, as an active ingredient, a verbenone derivative having a structure of Formula 1 or a pharmaceutically acceptable salt thereof.

The pharmaceutical composition and preventing or treating method of the present invention can be advantageously used, because they employ a derivative of verbenone derived from a natural substance that has an excellent activity of inhibiting neuronal death and oxidative stress and causes less toxicity and side effects.

In yet another aspect, the present invention is directed to a functional food or a food additive having an effect of preventing or treating a degenerative brain disease and comprising, as an active ingredient, a verbenone derivative having a structure of Formula 1 or a pharmaceutically acceptable salt thereof.

The functional food including the compound of the present invention can be used in various applications, including drugs, foods or beverages for the prevention of inflammation. Examples of the functional food of the present invention include various foods, candies, chocolates, beverages, gums, teas, vitamin complexes, health supplement foods, and the like, and it can be used in the forms of powders, granules, tablets, capsules or beverages.

A verbenone derivative that is contained as an active component in the functional food of the present invention has excellent effects on the protection of neuronal cells, the inhibition of oxidative stress and the inhibition of cytokine expression, as clearly demonstrated from the results of analysis of biological mechanisms as described below. Thus, it will be obvious to those skilled in the art that the use of the verbenone derivative in foods exhibits excellent effects.

The pharmaceutical composition comprising the compound according to the present invention can be formulated according to a conventional method. For example, it may be formulated in the form of powders, granules, tablets, capsules, suspensions, emulsions, syrups, aerosols, and the like for oral applications, agents for external applications, suppositories, and sterile injection solutions. Carriers, excipients and diluents that can be contained in the composition according to the present invention include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinylpyrrolidone, water, methylhydroxybenzoate, propylhydroxybenzoate, magnesium stearate, and mineral oil. A pharmaceutical composition comprising the compound according to the present invention is formulated using diluents or excipients, such as fillers, extenders, binders, wetting agents, disintegrants or surfactants, which are commonly used. Solid Formulations for oral administration include tablets, pills, powders, granules, capsules, etc. Such solid formulations are prepared by mixing the compound of present invention with at least one excipient, such as cotton, starch, calcium carbonate, sucrose, lactose, gelatin, etc. In addition to simple expedients, lubricants such as magnesium stearate, talc, etc. may also be added. Liquid formulations for oral administration, such as suspensions, oral solutions, emulsions, syrups, etc., may include simple diluents, e.g., water and liquid paraffin, as well as various excipients, e.g., wetting agents, sweeteners, aromatics, preservatives, etc. Formulations for parenteral administration include sterilized aqueous solutions, non-aqueous solvents, suspensions, emulsions, lyophilized agents, suppositories, etc. Non-aqueous solvents and suspensions may be prepared using propylene glycol, polyethylene glycol, vegetable oils such as olive oil, or injectable esters such as ethyloleate. As a base for suppositories, Witepsol, Macrogol, Tween 61, cacao fat, laurin fat, glycerogelatin, etc. may be used.

The preferred dosage of the compound of the present invention can be suitably selected depending on various factors, including the patient's condition and weight, the severity of disease, the type of drug, the route and period of administration, and can be suitably determined by a person skilled in the art. In order to achieve the desired effects, however, the compound of the present invention may be administered at a daily dose of from 0.01 mg/kg to 10 g/kg, and preferably 1 mg/kg to 1 g/kg. The compound may be administered in a single dose per day or in multiple doses per day. The dosage is not intended to limit the present invention in any way.

In addition, the present invention is directed to a health functional food for preventing or ameliorating a degenerative brain disease, the food comprising, as an active ingredient, a verbenone derivative having a structure of Formula 1 or a pharmaceutically acceptable salt thereof.

The health functional food including the compound of the present invention can be used in various applications, including drugs, foods and beverages for prevention and amelioration of degenerative brain diseases. Examples of the functional food of the present invention include various foods, beverages, gums, teas, vitamin complexes, health supplement foods, and the like, and it can be used in the form of powders, granules, tablets, capsules or beverages.

Examples of foods to which the compound of the present invention can be added include various candies, beverages, gums, teas, vitamin complexes, or health supplement foods, and the like.

The compound of the present invention may be added to foods or beverages for the prevention and amelioration of degenerative brain diseases. With respect to the content of the compound in food or beverage, the compound of the present invention may generally be added in an amount of 0.01-15 wt % based on the total weight of the health functional food of the present invention, and the compound of the present invention may be added in an amount of 0.02-10 g, and preferably 0.3-1 g, based on 100 ml of the health beverage composition of the present invention.

Providing that the health beverage composition of the present invention comprises the compound as an essential ingredient, there is no particular limitation in other liquid components of the beverage composition, and the composition may further comprise one or more additives, such as various flavors or natural carbohydrates which are commonly used in beverages. Examples of natural carbohydrates for such purposes include common sugars such as monosaccharides, for example, glucose, fructose and the like; disaccharides, for example, maltose, sucrose and the like; and polysaccharides, for example, dextrine, cyclodextrine and the like, and sugar alcohols such as xylitol, sorbitol, erythritol and the like. In addition to the foregoing, as the flavors, natural flavors (thaumatin, stevia compound (for example, Rebaudioside A, glycyrrhizin and the like), and synthetic flavors (saccharine, aspartame and the like) may be advantageously used. The content of the natural carbohydrate in the composition of the present invention is about 1-20 g, and preferably about 5-12 g, based on 100 ml of the composition.

In addition, the composition of the present invention may further contain various nutrients, vitamins, minerals (electrolytes), seasonings (artificial seasonings and natural seasonings), coloring agents and improving agents (cheese, chocolate and the like), pectic acid and salts thereof, alginic acid and salts thereof, organic acids, protective colloid thickeners, pH controllers, stabilizers, preservatives, glycerin, alcohols, carbonating agents used in carbonated beverages, and the like. In addition, the composition of the present invention may further contain fruit flesh for preparation of natural fruit juice beverages, fruit juice beverages and vegetable beverages. These additives may be used independently or in combination. Although the content of these additives in the composition of the present invention is not particularly important to the present invention, it is generally selected within the range of 0-20 parts by weight based on 100 parts by weight of the composition of the present invention.

The composition of the present invention comprises the compound in an amount 0.01 to 99 wt % based on the total weight of the composition. However, the composition of the present invention is not limited thereto, but may vary depending on the patient's condition, the type of diseases, and a degree of progress of diseases.

The composition comprising the compound according to the present invention may further comprise a suitable carrier, excipient or diluent that is generally used in the preparation of pharmaceutical composition

EXAMPLES

Hereinafter, the present invention will be described in further detail with reference to examples. However, it will be obvious to those skilled in the art that these examples are for illustrative purposes only and are not intended to limit the scope of the present invention.

Example 1: Preparation of Verbenone Derivatives

Reagents and Instruments

Reagent grade (1S)-(−)-verbenone, aldehydes, methylchloromethylether (MOM-Cl), diisopropylethylamine (DIPEA), potassium hydroxide (KOH), and sodium methoxide (NaOCH$_3$) were commercially purchased. All the purchased reagents and solvents had high purity, and were used directly without additional purification, except for dichloromethane distilled with calcium hydroxide. Unless specified otherwise, a reaction was performed in a vacuum-flame dried glassware under a dry nitrogen atmosphere. Thin-layer chromatography (TLC) was performed using Merck silica gel 60 F$_{254}$ that is visualized by UV light, and column chromatography was performed using silica gel (E.Merck silica gel, 70-230, 230-400 mesh). $^1$H-NMR and $^{13}$C-NMR spectra were measured using an instrument (Varian) at 500 MHz, and chemical shifts were reported in ppm from tetramethysilane (TMS) as an internal standard (CDCl$_3$: d 7.26 ppm), and coupling constant was recorded in Hertz. Multiplicity was recorded using the following abbreviations: singlet (s), doublet (d), doublet of doublet (dd), doublet of doublet of doublet (ddd), triplet (t), triplet of doublet (td), doublet of triplet (dt), quartet (q), multiplet (m), and broad (br). High-resolution mass spectra (HRMS) were recorded with an instrument (Waters Q-TOF micro mass spectrometer), and optical rotation was measured with an instrument (JASCO polarimeter mode 1P-2000) at 589 nm. All compounds were measured by reverse-phase HPLC under the following conditions, and the purities thereof were >95%: Method 1 (Solvent A: water, Solvent B: acetonitrile), flow rate: 0.2 ml/min: 90% of B in 20 min; method 2 (Solvent A: water, Solvent B: acetonitrile), flow rate: 1.0 ml/min: From 40% of B to 100% in 40 min. Fetal bovine serum (FBS) used was purchased from a company (Hyclone, Logan, Utah), and neurobasal medium (NBM) and B27 supplement used were purchased from a company (Invitrogen, Carlsbad, Calif.). In addition, all chemicals and reagents used were purchased from a company (Sigma—Aldrich, St. Louis, Mo.).

Example 1-1: Preparation of (1S,5R)-4-(4-(methoxymethoxy)styryl)-6,6-dimethylbicyclo[3.1.1] hept-3-en-2-one (Compound 2a)

In order to obtain diene from (1S)-(−)-verbenone by aldol condensation, (1S)-(−)-verbenone 1 (200 mg, 1.33 mmol) and 4-(methoxymethoxy)benzaldehyde (332 mg, 2.00 mmol) were stirred in MeOH (7 mL), and treated with KOH (149 mg, 2.66 mmol). The reaction mixture was stirred at 60° C. for 6 hours, and cooled to room temperature. A small amount of water was added to the mixture which was then allowed to stand at room temperature for 24 hours. Then, the mixture was concentrated under reduced pressure to obtain a yellow product, which was then purified by silica gel column chromatography, thereby obtaining (1S,5R)-4-(4-(methoxymethoxy)styryl)-6,6-dimethylbicyclo[3.1.1]hept-3-en-2-one (compound 2a) as a yellow solid. (353 mg, 89% yield). The obtained compound was used as a sample in the Experimental Examples below.

mp 88-90° C.;

$[a]^{20}{}_D$ −211.6° (c1.0, MeOH);

$^1$H-NMR (CDCl$_3$, 500 MHz): d7.45 (d, J=8.80 Hz, 2H), 7.04 (d, J=8.80 Hz, 2H), 6.81-6.92 (m, 2H), 5.90 (s, 1H), 5.20 (s, 2H), 3.48 (s, 3H), 3.03-3.17 (m, 1H), 2.91 (dt, J=9.48, 5.53 Hz, 1H), 2.72 (t, J=5.62 Hz, 1H), 2.12 (d, J=9.29 Hz, 1H), 1.58 (s, 3H), 1.01 (s, 3H);

$^{13}$C-NMR (CDCl$_3$, 75 MHz); d 204.25, 164.57, 158.00, 134.51, 129.75, 128.73, 125.62, 121.83, 116.44, 94.171, 58.09, 56.09, 52.78, 43.59, 39.98, 26.72, 22.10

HRMS: calculated value C$_{17}$H$_{18}$O$_2$ (M−H) 253.1229, measured value 253.1221.

HPLC analytical result: (method 1) 100.0% (t$_R$=3.67 min).

Example 1-2: Preparation of (1S,5R)-4-(3-methoxy-4,5-bis(methoxystyryl)styryl)-6,6-dimethylbicyclo[3.1.1]hept-3-en-2-one (compound 2f)

Using a method similar to the preparation method of compound 2a, (1S,5R)-4-(3-methoxy-4,5-bis(methoxymethoxy)styryl)-6,6-dimethylbicyclo[3.1.1]hept-3-en-2-one (compound 2f) showing the following characteristics were prepared (yield: 90%). The obtained compound was used as a sample in the Experimental Examples below.

$^1$H—

NMR (CDCl$_3$, 500 MHz); d6.94 (d, J=1.96 Hz, 1H), 6.84 (s, 2H), 6.78 (d, J=1.71 Hz, 1H), 5.92 (s, 1H), 5.22 (s, 2H), 5.15 (s, 2H), 3.89 (s, 3H), 3.60 (s, 3H), 3.52 (s, 3H), 3.09 (t, J=5.75 Hz, 1H), 2.90 (dt, J=9.48, 5.53 Hz, 1H), 2.72 (td, J=5.75, 1.47 Hz, 1H), 2.10 (d, J=9.29 Hz, 1H), 1.57 (s, 3H), 1.00 (s, 3H);

$^{13}$C-NMR (CDCl$_3$, 75 MHz); d203.92, 164.02, 153.63, 151.19, 136.64, 134.76, 132.10, 126.91, 122.43, 108.91, 104.88, 98.37, 95.33, 58.19, 57.11, 56.07, 52.70, 43.78, 39.93, 26.70, 22.11.

Example 1-3: Preparation of (1S,5R)-4-(4-hydroxystyryl)-6,6-dimethylbicyclo[3.1.1]hept-3-en-2-one (Compound 3a)

In order to obtain diene from (1S)-(−)-verbenone by aldol condensation, 10% HCl was added dropwise to a stirred solution of compound 2a (200 mg, 0.67 mmol) in MeOH (3 mL), and the reaction mixture was allowed to stand overnight until completion of the reaction. Then, saturated NaHCO$_3$ was added to the reaction mixture, which was then extracted with ethyl acetate and dried with anhydrous MgSO$_4$. The remaining material was purified by column chromatography to afford (1S,5R)-4-(4-hydroxystyryl)-6,6-dimethylbicyclo[3.1.1]hept-3-en-2-one (compound 3a) as a yellow solid showing the following characteristics. The obtained compound was used as a sample in the Experimental Examples below (162 mg, 95% yield).

mp 88-90° C.

$[a]^{20}{}_D$ –211.6° (c1.0, MeOH);

$^1$H-NMR (CDCl$_3$, 500 MHz); d7.40 (d, J=8.56 Hz, 2H), 6.78-6.92 (m, 4H), 6.45 (br. s., 1H), 5.91 (s, 1H), 3.12 (t, J=5.75 Hz, 1H), 2.88-2.95 (m, 1H), 2.74 (t, J=5.62 Hz, 1H), 2.13 (d, J=9.29 Hz, 1H), 1.58 (s, 3H), 1.02 (s, 3H);

$^{13}$C-NMR (CDCl$_3$, 75 MHz); d205.14, 165.56, 157.32, 135.24, 129.13, 128.51, 124.89, 121.29, 116.00, 58.10, 53.22, 43.86, 40.23, 26.79, 22.15;

HRMS calculated value C$_{17}$H$_{18}$O$_2$ (M−H) 253.1229, measured value 253.1221;

HPLC analytical result: (method 1) 100.0% ($t_R$=3.67 min).

Example 1-4: Preparation of (1S,5R)-4-(4-hydroxy-2-methoxystyryl)-6,6-dimethylbicyclo[3.1.1]hept-3-en-2-one (Compound 3b)

Using a method similar to the preparation method of compound 3a, (1S,5R)-4-(4-hydroxy-2-methoxystyryl)-6,6-dimethylbicyclo[3.1.1]hept-3-en-2-one (3b) was obtained as a yellow solid showing the following characteristics (yield: 97%). The obtained compound was used as a sample in the Experimental Examples below.

mp 78-80° C.;

$[a]^{20}{}_D$ –140.0° (c1.0, MeOH);

$^1$H-NMR (CDCl$_3$, 500 MHz); d7.45 (d, J=8.07 Hz, 1H), 7.24 (d, J=16.63 Hz, 1H), 6.88 (d, J=16.38 Hz, 1H), 6.42-6.48 (m, 2H), 5.88 (s, 1H), 3.86 (s, 3H) 5.64 (br. s., 1H), 3.16 (t, J=5.75 Hz, 1H), 2.91 (dt, J=9.35, 5.59 Hz, 1H), 2.72 (td, J=5.60 Hz, 1H), 2.12 (d, J=9.29 Hz, 1H), 1.58 (s, 3H), 1.02 (s, 3H);

$^{13}$C-NMR (CDCl$_3$, 75 MHz); d 205.53, 166.76, 159.17, 158.94, 130.48, 128.48, 124.75, 120.62, 117.50, 108.19, 99.19, 58.10, 55.53, 53.25, 43.87, 40.33, 26.80, 22.16;

HRMS calculated value C$_{18}$H$_{20}$O$_3$ (M+H) 285.1491, measured value 285.1480;

HPLC analytical result: (method 1) 99.4% ($t_R$=3.80 min).

Example 1-5: Preparation of (1S,5R)-4-(3,4-dihydroxystyryl)-6,6-dimethylcyclo[3.1.1]hept-3-en-2-one (Compound 3c)

Using a method similar to the preparation method of compound 3a, (1S,5R)-4-(3,4-dihydroxystyryl)-6,6-dimethylbicyclo[3.1.1]hept-3-en-2-one (3c) was obtained as a yellow solid showing the following characteristics (yield: 84%). The obtained compound was used as a sample in the Experimental Examples below.

mp 68-70° C.;

$[a]^{20}{}_D$ –208.6° (c1.0, MeOH);

$^1$H-NMR (CDCl$_3$, 500 MHz); d7.13 (s, 1H), 6.70-6.96 (m, 4H), 5.92 (s, 1H), 3.12 (t, J=5.50 Hz, 1H), 2.86-2.95 (m, 1H), 2.71-2.81 (m, 1H), 2.14 (d, J=9.54 Hz, 1H), 1.58 (s, 3H), 1.00 (s, 3H);

$^{13}$C-NMR (CDCl$_3$, 75 MHz); d206.39, 166.93, 146.23, 144.51, 136.47, 128.75, 124.62, 121.91, 120.72, 115.38, 113.17, 60.55, 58.04, 53.84, 44.01, 40.55, 26.78, 22.12;

HRMS calculated value C$_{17}$H$_{18}$O$_3$ (M−H) 269.1178, measured value 269.1169;

HPLC analytical result: (method 1) 100% ($t_R$=3.47 min).

Example 1-6: Preparation of (1S,5R)-4-(3-bromo-4-hydroxystyryl)-6,6-dimethylcyclo[3.1.1]hept-3-en-2-one (Compound 3d)

Using a method similar to the preparation method of compound 3a, (1S,5R)-4-(3-bromo-4-hydroxystyryl)-6,6-dimethylbicyclo[3.1.1]hept-3-en-2-one (compound 3d) was obtained as a yellow solid showing the following characteristics (yield: 95%). The obtained compound was used as a sample in the Experimental Examples below.

mp 238-240° C.;

$[a]^{20}{}_D$ –181.4° (c1.0, MeOH);

$^1$H-NMR (CD$_3$OD, 500 MHz); d7.75 (d, J=2.20 Hz, 1H), 7.45 (dd, J=1.96, 8.56 Hz, 1H), 7.02 (d, J=16.50 Hz, 1H), 6.97 (d, J=16.50 Hz, 1H), 6.92 (d, J=8.56 Hz, 1H), 5.90 (s, 1H), 3.24 (t, J=5.99 Hz, 1H), 2.97 (td, J=5.59, 9.35 Hz, 1H), 2.62 (dt, J=1.50, 6.00 Hz, 1H), 2.05 (d, J=9.54 Hz, 1H), 1.60 (s, 3H), 0.98 (s, 3H);

$^{13}$C-NMR (CD$_3$OD, 75 MHz): d203.02, 165.13, 155.42, 134.47, 132.29, 129.42, 128.79, 125.75, 121.59, 117.11, 110.36, 58.16, 52.33, 43.30, 26.83, 22.43;

HRMS calculated value C$_{17}$H$_{17}$BrO$_2$ (M+H) 333.0490, measured value 333.0479;

HPLC analytical result: (method 1) 98.9% ($t_R$=3.91 min).

Example 1-7: Preparation of (1S,5R)-4-(4-hydroxy-2,6-dimethoxystyryl)-6,6-dimethylcyclo[3.1.1]hept-3-en-2-one (Compound 3e)

Using a method similar to the preparation method of compound 3a, (1S,5R)-4-(4-hydroxy-2,6-dimethoxystyryl)-6,6-dimethylbicyclo[3.1.1]hept-3-en-2-one (compound 3e) was obtained as a yellow solid showing the following characteristics (yield: 94%). The obtained compound was used as a sample in the Experimental Examples below.

mp 216-218° C.;

$[a]^{20}{}_D$ –175.4° (c1.0, MeOH);

$^1$H-NMR (DMSO-d$_6$, 500 MHz); d7.28 (d, J=16.50 Hz, 1H), 7.23 (d, J=16.50 Hz, 1H), 6.12 (s, 2H), 5.73 (s, 1H), 3.80 (s, 6H), 3.10 (t, J=5.38 Hz, 1H), 2.89 (td, J=5.50, 9.05 Hz, 1H), 2.53 (t, J=5.50 Hz, 1H), 1.93 (d, J=9.29 Hz, 1H), 1.53 (s, 3H), 0.91 (s, 3H);

$^{13}$C-NMR (DMSO-d$_6$, 75 MHz); d202.56, 166.66, 160.48, 160.27, 126.68, 126.11, 119.22, 104.67, 92.17, 57.50, 55.71, 55.67, 51.67, 42.59, 26.42, 21.96;

HRMS calculated value C$_{19}$H$_{22}$O$_4$ (M+H) 315.1596, measured value 315.1583;

HPLC analytical result: (method 1) 99.3% ($t_R$=3.70 min).

Example 1-8: Preparation of (1S,5R)-4-(3,4-dihydroxy-5-methoxystyryl)-6,6-dimethylbicyclo[3.1.1]hept-3-en-2-one (Compound 3f)

Using a method similar to the preparation method of compound 3a, (1S,5R)-4-(3,4-dihydroxy-5-methoxystyryl)-6,6-dimethylbicyclo[3.1.1]hept-3-en-2-one (3f) was obtained as a yellow solid showing the following characteristics (yield: 92%). The obtained compound was used as a sample in the Experimental Examples below.

mp 168-170° C.;

$[a]^{20}{}_D$ –158.8000° (c1.0, MeOH);

$^1$H-NMR (CDCl$_3$, 500 MHz) d6.78-6.82 (m, 3H), 6.64 (d, J=1.47 Hz, 1H), 5.82-6.01 (m, 3H), 3.92 (s, 3H), 3.10 (t, J=5.62 Hz, 1H), 2.91 (dt, J=9.35, 5.59 Hz, 1H), 2.74 (td, J=5.69, 1.59 Hz, 1H), 2.12 (d, J=9.29 Hz, 1H), 2.04 (s, 2H), 1.58 (s, 3H), 1.01 (s, 3H);

$^{13}$C— NMR (CDCl$_3$, 75 MHz); d204.92, 165.07, 147.23, 144.24, 135.54, 134.13, 128.07, 125.50, 121.62, 108.6 3, 58.08, 56.25, 53.12, 43.75, 40.18, 26.78, 22.16;

HRMS calculated value C$_{18}$H$_{20}$O$_4$ (M+H) 301.1440, measured value 301.1453;

HPLC analytical result: (method 1) 100% ($t_R$=3.46 min).

Example 1-9: Preparation of (1S,5R)-4-(3-hydroxystyryl)-6,6-dimethylbicyclo[3.1.1]hept-3-en-2-one (Compound 2g)

Using a method similar to the preparation method of compound 3a, (1S,5R)-4-(3-hydroxystyryl)-6,6-dimethylbicyclo[3.1.1]hept-3-en-2-one (compound 3g) was obtained as a yellow solid showing the following characteristics (yield: 98%). The obtained compound was used as a sample in the Experimental Examples below.

mp 106-108° C.;
$[a]^{20}_D$ -176.6° (c1.0, MeOH);
$^1$H-NMR (CDCl$_3$, 500 MHz); d7.21-7.26 (m, 1H), 7.01-7.05 (m, 2H), 6.92 (d, J=16.50 Hz, 1H), 6.88 (d, J=16.50 Hz, 1H), 6.83-6.86 (m, 1H), 6.46 (s, 1H), 5.96 (s, 1H), 3.11 (t, J=5.75 Hz, 1H), 2.93 (td, J=5.53, 9.48 Hz, 1H), 2.77 (dt, J=1.59, 5.69 Hz, 1H), 2.14 (d, J=9.29 Hz, 1H), 1.59 (s, 3H), 1.01 (s, 3H);
$^{13}$C-NMR (CDCl$_3$, 75 MHz); d205.19, 165.18, 156.53, 137.42, 135.36, 130.03, 127.44, 122.37, 120.19, 116.68, 113.65, 58.17, 53.39, 43.89, 40.28, 26.77, 22.14;
HRMS calculated value C$_{17}$H$_{18}$O$_2$ (M−H) 253.1229, measured value 253.1228;
HPLC analytical result: (method 2) 99.3% ($t_R$=3.73 min).

Example 1-10: Preparation of (1S,5R)-4-(2-hydroxystyryl)-6,6-dimethylbicyclo[3.1.1]hept-3-en-2-one (Compound 3h)

Using a method similar to the preparation method of compound 3a, (1S,5R)-4-(2-hydroxystyryl)-6,6-dimethylbicyclo[3.1.1]hept-3-en-2-one (compound 3h) was obtained as a yellow solid showing the following characteristics (yield: 100%). The obtained compound was used as a sample in the Experimental Examples below.

mp 140-142° C.;
$[a]^{20}_D$ -296.6° (c1.0, MeOH);
$^1$H-NMR (CD$_3$OD, 500 MHz); d7.56 (dd, J=1.59, 7.70 Hz, 1H), 7.42 (d, J=16.14 Hz, 1H), 7.15 (dd, J=1.59, 15.53 Hz, 1H), 7.13 (d, J=16.38 Hz, 1H), 6.80-6.87 (m, 2H), 5.89 (s, 1H), 3.25 (t, J=5.87 Hz, 1H), 2.99 (dt, J=5.53, 9.48 Hz, 1H), 2.65 (td, J=1.71, 5.75 Hz, 1H), 2.08 (d, J=9.29 Hz, 1H), 1.61 (s, 3H), 1.01 (s, 3H);
$^{13}$C-NMR (CD$_3$OD, 75 MHz); d207.46, 169.09, 157.56, 133.10, 131.67, 128.67, 127.63, 124.55, 122.03, 121.07, 117.05, 59.62, 54.52, 45.29, 41.45, 27.19, 22.58;
HRMS calculated value C$_{17}$H$_{18}$O$_2$ (M−H) 253.1229, measured value 253.1218;
HPLC analytical result: (method 1) 99.4% ($t_R$=3.80 min).

Example 1-11: Preparation of (1S,5R)-4-(2-hydroxy-4-methoxystyryl)-6,6-dimethylbicyclo[3.1.1]hept-3-en-2-one (Compound 3i)

Using a method similar to the preparation method of compound 3a, (1S,5R)-4-(2-hydroxy-4-methoxystyryl)-6,6-dimethylbicyclo[3.1.1]hept-3-en-2-one (compound 3i) was obtained as a yellow gel showing the following characteristics (yield: 96%). The obtained compound was used as a sample in the Experimental Examples below.

$[a]^{20}_D$ -91.8° (c1.0, MeOH);
$^1$H-NMR (CDCl$_3$, 500 MHz); d8.46 (br.s., 1H), 7.37 (d, J=8.56 Hz, 1H), 7.23 (d, J=16.50 Hz, 1H), 7.17 (d, J=16.00 Hz, 1H), 6.42-6.55 (m, 2H), 6.04 (s, 1H), 3.78 (s, 3H), 3.20 (t, J=5.38 Hz, 1H), 2.88-2.98 (m, 1H), 2.76 (t, J=5.14 Hz, 1H), 2.17 (d, J=9.54 Hz, 1H), 1.59 (s, 3H), 1.05 (s, 3H);
$^{13}$C-NMR (CDCl$_3$, 75 MHz); d206.56, 167.94, 161.72, 156.99, 132.26, 130.09, 125.37, 119.93, 116.29, 106.90, 101.73, 57.96, 55.28, 53.74, 43.85, 40.60, 26.76, 22.13;
HRMS calculated value C$_{18}$H$_{20}$O$_3$ (M+H) 285.1491, measured value 285.1494;
HPLC analytical result: (method 1) 99.2% ($t_R$=3.75 min).

Example 1-12: Preparation of (1S,5R)-6,6-dimethyl-4-styrylbicyclo[3.1.1]hept-3-en-2-one (Compound 4a)

Using a method similar to the preparation method of compound 2a, (1S,5R)-6,6-dimethyl-4-styrylbicyclo[3.1.1]hept-3-en-2-one (compound 4a) was obtained as a yellow gel showing the following characteristics (yield: 92%). The obtained compound was used as a sample in the Experimental Examples below.

$[a]^{20}_D$ -91.8° (c1.0, MeOH);
$^1$H-NMR (CDCl$_3$, 500 MHz); d7.50 (d, J=7.09 Hz, 2H), 7.35-7.40 (m, 2H), 7.33 (d, J=7.34 Hz, 1H), 6.97 (d, J=16.00 Hz, 1H), 6.92 (d, J=16.00 Hz, 1H), 5.94 (s, 1H), 3.12 (td, J=1.47, 5.87 Hz, 1H), 2.93 (dt, J=5.62, 9.54 Hz, 1H), 2.74 (td, J=1.71, 5.75 Hz, 1H), 2.13 (d, J=9.29 Hz, 1H), 1.59 (s, 3H), 1.02 (s, 3H);
$^{13}$C-NMR (CDCl$_3$, 75 MHz); d204.13, 164.23, 135.99, 134.96, 129.15, 128.88, 127.42, 127.35, 122.66, 58.23, 52.87, 43.76, 40.03, 26.78, 22.16;
HRMS calculated value C$_{17}$H$_{18}$O (M+H) 239.1436, measured value 239.1426;
HPLC analytical result: (method 1) 95.0% ($t_R$=4.82 min).

Example 1-13: Preparation of (1S,5R)-4-(4-fluorostyryl)-6,6-dimethylcyclo[3.1.1]hept-3-en-2-one (Compound 4b)

Using a method similar to the preparation method of compound 2a, (1S,5R)-4-(4-fluorostyryl)-6,6-dimethylcyclo[3.1.1]hept-3-en-2-one (compound 4b) was obtained as a yellow gel showing the following characteristics (yield: 92%). The obtained compound was used as a sample in the Experimental Examples below.

$[a]^{20}_D$ -33.2° (c1.0, MeOH);
$^1$H-NMR (CDCl$_3$, 500 MHz); d7.46-7.51 (m, 2H), 7.04-7.09 (m, 2H), 6.90 (d, J=17.00 Hz, 1H), 6.86 (d, J=16.50 Hz, 1H), 5.93 (s, 1H), 3.10 (td, J=1.35, 5.81 Hz, 1H), 2.92 (dt, J=5.62, 9.29 Hz, 1H), 2.74 (td, J=1.71, 5.75 Hz, 1H), 2.12 (d, J=9.29 Hz, 1H), 1.59 (s, 3H), 1.02 (s, 3H);
$^{13}$C-NMR (CDCl$_3$, 75 MHz); d204.04, 164.03, 162.13, 133.62, 132.21, 129.04, 127.15, 122.61, 116.02, 58.17, 52.83, 43.72, 39.99, 26.73, 22.12;
HRMS calculated value C$_{17}$H$_{17}$FO (M+H) 257.1342, measured value 257.1343;
HPLC analytical result: (method 1) 90.6% ($t_R$=4.52 min).

Example 1-14: Preparation of (1S,5R)-4-(4-methoxystyryl)-6,6-dimethylbicyclo[3.1.1]hept-3-en-2-one (Compound 4c)

Using a method similar to the preparation method of compound 2a, (1S,5R)-4-(4-methoxystyryl)-6,6-dimethylbicyclo[3.1.1]hept-3-en-2-one (compound 4c) was obtained as a yellow solid showing the following characteristics (yield: 90%). The obtained compound was used as a sample in the Experimental Examples below.

mp 138-140° C.;
$[a]^{20}_D$ -172.0° (c1.0, MeOH);

¹H-NMR (CDCl₃, 500 MHz); d7.46 (d, J=8.80 Hz, 2H), 6.91 (d, J=9.05 Hz, 2H), 6.90 (d, J=15.90 Hz, 1H), 6.84 (d, J=16.50 Hz, 1H), 5.90 (s, 1H), 3.85 (s, 3H), 3.12 (td, J=1.35, 5.81 Hz, 1H), 2.92 (dt, J=5.53, 9.48 Hz, 1H), 2.73 (td, J=1.71, 5.75 Hz, 1H), 2.13 (d, J=9.54 Hz, 1H), 1.59 (s, 3H), 1.03 (s, 3H);
¹³C-NMR (CDCl₃, 75 MHz); d204.17, 164.63, 160.50, 134.64, 128.83, 128.78, 125.25, 121.66, 114.35, 58.17, 55.34, 52.74, 43.76, 39.99, 26.76, 22.15;
HRMS calculated value $C_{18}H_{20}O_2$ (M+H) 269.1542, measured value 269.1549;
HPLC analytical result: (method 1) 100% ($t_R$=4.58 min).

Example 1-15: Preparation of (1S,5R)-4-(2-(biphenyl-4-yl)vinyl)-6,6-dimethylcyclo[3.1.1]hept-3-en-2-one (Compound 4d)

Using a method similar to the preparation method of compound 2a, (1S,5R)-4-(2-(biphenyl-4-yl)vinyl)-6,6-dimethylbicyclo[3.1.1]hept-3-en-2-one (compound 4d) was obtained as a yellow solid showing the following characteristics (yield: 92%). The obtained compound was used as a sample in the Experimental Examples below.
mp 148-150° C.;
$[a]^{20}_D$ −152.4° (c1.0, MeOH);
¹H-NMR (CDCl₃, 500 MHz); d7.55-7.65 (m, 6H), 7.45 (t, J=7.58 Hz, 2H), 7.34-7.39 (m, 1H), 7.01 (d, J=16.50 Hz, 1H), 6.96 (d, J=16.50 Hz, 1H), 5.95 (s, 1H), 3.14 (t, J=5.75 Hz, 1H), 2.94 (dt, J=5.50, 9.54 Hz, 1H), 2.75 (t, J=5.62 Hz, 1H), 2.14 (d, J=9.29 Hz, 1H), 1.60 (s, 3H), 1.03 (s, 3H);
¹³C-NMR (CDCl₃, 75 MHz); d204.12, 164.23, 141.86, 140.23, 134.99, 134.50, 128.87, 127.84, 127.69, 127.51, 127.38, 126.94, 122.65, 58.24, 52.86, 43.77, 40.02, 26.79, 22.18;
HRMS calculated value $C_{23}H_{22}O$ (M+H) 315.1749, measured value 315.1737;
HPLC analytical result: (method 1) 100% ($t_R$=6.35 min).

Example 1-16: Preparation of (1S,5R)-4-(4-(1H-pyrrol-1-yl)styryl)-6,6-dimethylbicyclo[3.1.1]hept-3-en-2-one (Compound 4e)

Using a method similar to the preparation method of compound 2a, (1S,5R)-4-(4-(1H-pyrrol-1-yl)styryl)-6,6-dimethylbicyclo[3.1.1]hept-3-en-2-one compound (4e) was obtained as a yellow solid showing the following characteristics (yield: 41%). The obtained compound was used as a sample in the Experimental Examples below.
mp 146-148° C.;
$[a]^{20}_D$ −142.4° (c1.0, MeOH);
¹H-NMR (CDCl₃, 500 MHz); d7.55 (d, J=8.56 Hz, 2H), 7.39 (d, J=8.56 Hz, 2H), 7.12 (t, J=2.20 Hz, 2H), 6.95 (d, J=16.00 Hz, 1H), 6.91 (d, J=16.00 Hz, 1H), 6.36 (t, J=2.20 Hz, 2H), 5.94 (s, 1H), 3.12 (t, J=5.75 Hz, 1H), 2.93 (td, J=5.59, 9.35 Hz, 1H), 2.74 (dt, J=1.71, 5.75 Hz, 1H), 2.13 (d, J=9.29 Hz, 1H), 1.59 (s, 3H), 1.03 (s, 3H);
¹³C-NMR (CDCl₃, 75 MHz); d203.97, 164.03, 140.92, 133.78, 133.21, 128.57, 127.14, 122.61, 120.25, 118.95, 110.94, 58.19, 25.79, 43.72, 39.97, 26.75, 22.14;
HRMS calculated value $C_{21}H_{21}NO$ (M+H) 304.1701, measured value 304.1691;
HPLC analytical result: (method 1) 94.7% ($t_R$=5.10 min).

Example 1-17: Preparation of (1S,5R)-4-(3,4-dimethoxystyryl)-6,6-dimethylbicyclo[3.1.1]hept-3-en-2-one (Compound 4f)

Using a method similar to the preparation method of compound 2a, (1S,5R)-4-(3,4-dimethoxystyryl)-6,6-dimethylbicyclo[3.1.1]hept-3-en-2-one (Compound 4f) was obtained as a yellow gel showing the following characteristics (yield: 92%). The obtained compound was used as a sample in the Experimental Examples below.
$[a]^{20}_D$ −111.2° (c1.0, MeOH);
¹H-NMR (CDCl₃, 500 MHz); d7.02-7.09 (m, 2H), 6.89 (d, J=16.00 Hz, 1H), 6.86 (d, J=7.00 Hz, 1H), 6.83 (d, J=16.50 Hz, 1H), 5.91 (s, 1H), 3.93 (s, 3H), 3.91 (s, 3H), 3.11 (t, J=5.75 Hz, 1H), 2.91 (dtd, J=1.47, 5.56, 9.41 Hz, 1H), 2.72 (tt, J=1.74, 5.72 Hz, 1H), 2.11 (d, J=9.29 Hz, 1H), 1.58 (s, 3H), 1.02 (s, 3H);
¹³C-NMR (CDCl₃, 75 MHz); d204.03, 164.46, 150.28, 149.30, 134.89, 129.10, 125.42, 121.75, 111.24, 109.29, 58.19, 55.94, 52.69, 43.82, 39.96, 26.76, 22.15;
HRMS calculated value $C_{19}H_{22}O_3$ (M+H) 299.1647, measured value 299.1657;
HPLC analytical result: (method 2) 97.9% ($t_R$=9.19 min).

Example 1-18: Preparation of (1S,5R)-4-(3,5-dimethoxystyryl)-6,6-dimethylbicyclo[3.1.1]hept-3-en-2-one (Compound 4)

Using a method similar to the preparation method of compound 2a, (1S,5R)-4-(3,5-dimethoxystyryl)-6,6-dimethylbicyclo[3.1.1]hept-3-en-2-one (compound 4g) was obtained as a yellow gel showing the following characteristics (yield: 90%). The obtained compound was used as a sample in the Experimental Examples below.
$[a]^{20}_D$ −94.2° (c1.0, MeOH);
¹H-NMR (CDCl₃, 500 MHz); d6.93 (d, J=16.00 Hz, 1H), 6.85 (d, J=16.00 Hz, 1H), 6.65 (d, J=2.20 Hz, 2H), 6.45 (t, J=2.20 Hz, 1H), 5.94 (s, 1H), 3.82 (s, 6H), 3.10 (t, J=5.75 Hz, 1H), 2.92 (dt, J=5.62, 9.54 Hz, 1H), 2.74 (td, J=1.59, 5.69 Hz, 1H), 2.12 (d, J=9.29 Hz, 1H), 1.58 (s, 3H), 1.02 (s, 3H);
¹³C-NMR (CDCl₃, 75 MHz); d204.04, 163.03, 161.03, 137.88, 134.93, 127.83, 122.81, 105.32, 101.51, 58.19, 55.40, 52.82, 43.73, 39.99, 26.73, 22.12;
HRMS calculated value $C_{19}H_{22}O_3$ (M+H) 299.1647, measured value 299.1662;
HPLC analytical method: (method 1) 100% ($t_R$=4.58 min).

Example 1-19: Preparation of (1S,5R)-4-(2,5-dimethoxystyryl)-6,6-dimethylbicyclo[3.1.1]hept-3-en-2-one (Compound 4 h)

Using a method similar to the preparation method of compound 2a, (1S,5R)-4-(2,5-dimethoxystyryl)-6,6-dimethylbicyclo[3.1.1]hept-3-en-2-one (compound 4 h) was obtained as a yellow gel showing the following characteristics (yield: 93%). The obtained compound was used as a sample in the Experimental Examples below.
$[a]^{20}_D$ −94.8° (c1.0, MeOH);
¹H-NMR (CDCl₃, 500 MHz); d7.29 (d, J=16.38 Hz, 1H), 7.11 (d, J=2.69 Hz, 1H), 6.95 (d, J=16.14 Hz, 1H), 6.81-6.88 (m, 2H), 5.92 (s, 1H), 3.84 (s, 3H), 3.81 (s, 3H), 3.16 (dt, J=1.50, 6.00 Hz, 1H), 2.91 (td, J=5.62, 9.29 Hz, 1H), 2.72 (dt, J=1.71, 5.75 Hz, 1H), 2.11 (d, J=9.29 Hz, 1H), 1.58 (s, 3H), 1.02 (s, 3H);
¹³C-NMR (CDCl₃, 75 MHz); d204.16, 164.83, 153.74, 152.04, 129.50, 127.74, 125.62, 122.37, 115.85, 112.34, 111.85, 58.24, 56.13, 52.76, 43.76, 40.03, 26.76, 22.15;
HRMS calculated value $C_{19}H_{22}O_3$ (M+H) 299.1647, measured value 299.1650;
HPLC analytical result: (method 1) 96.4% ($t_R$=4.69 min).

Example 1-20: Preparation of (1S,5R)-4-(5-bromo-2-methoxystyryl)-6,6-dimethylbicyclo[3.1.1]hept-3-en-2-one (Compound 4i)

Using a method similar to the preparation method of compound 2a, (1S,5R)-4-(5-bromo-2-methoxystyryl)-6,6- dimethylbicyclo[3.1.1]hept-3-en-2-one (compound 4i) was obtained as a yellow gel showing the following characteristics (yield: 97%). The obtained compound was used as a sample in the Experimental Examples below.

$[\alpha]^{20}_D$ –71.6° (c1.0, MeOH);

$^1$H-NMR (CDCl$_3$, 500 MHz); d7.66 (s, 1H), 7.36 (dd, J=2.45, 8.80 Hz, 1H), 7.20 (d, J=16.38 Hz, 1H), 6.95 (d, J=16.14 Hz, 1H), 6.77 (d, J=8.80 Hz, 1H), 5.93 (s, 1H), 3.87 (s, 3H), 3.12 (t, J=5.62 Hz, 1H), 2.91 (dt, J=5.35, 9.60 Hz, 1H), 2.73 (t, J=5.14 Hz, 1H), 2.11 (d, J=9.29 Hz, 1H), 1.58 (s, 3H), 1.01 (s, 3H);

$^{13}$C-NMR (CDCl$_3$, 75 MHz); d203.97, 164.31, 156.40, 132.53, 129.53, 128.69, 128.09, 127.04, 122.89, 113.28, 112.75, 58.22, 55.77, 52.76, 43.71, 39.98, 26.73, 22.11;

HRMS calculated value C$_{18}$H$_{19}$BrO$_2$ (M+H) 347.0647, measured value 347.0651;

HPLC analytical result: (method 1) 99.0% ($t_R$=6.23 min).

Example 1-21: Preparation of (1S,5R)-6,6-dimethyl-4-(E)-2-(pyridin-2-yl)vinyl)bicyclo[3.1.1]hept-3-en-2-one (Compound 5a)

In order to obtain diene from (1S)-(–)-verbenone by aldol condensation, (1S)-(–)-verbenone 1 (200 mg, 1.33 mmol) and 2-pyridinecarboxaldehyde (171 mg, 1.60 mmol) were stirred in MeOH (7 mL), and treated with NaOCH$_3$ (25 wt % solution in MeOH). The reaction mixture was stirred at 60° C. for 6 hours, and cooled to room temperature. A small amount of water was added to the mixture which was then allowed to stand at room temperature for 24 hours. Then, the mixture was concentrated under reduced pressure, and purified by column chromatography, thereby obtaining (1S,5R)-6,6-dimethyl-4-((E)-2-(pyridin-2-yl)vinyl)bicyclo[3.1.1]hept-3-en-2-one (compound 5a) as a yellow syrup showing the following characteristics (258 mg, 81% yield). The obtained compound was used as a sample in the Experimental Examples below.

$[\alpha]^{20}_D$ –102.0000° (c1.0, MeOH);

$^1$H—

NMR (CDCl$_3$, 500 MHz); d8.60 (dd, J=4.77, 0.61 Hz, 1H), 7.67 (td, J=7.70, 1.71 Hz, 1H), 7.45 (d, J=15.90 Hz, 1H), 7.39 (d, J=7.83 Hz, 1H), 7.19 (ddd, J=7.52, 4.83, 0.86 Hz, 1H), 6.96 (d, J=15.89 Hz, 1H), 6.02 (s, 1H), 3.08-3.14 (m, 1H), 2.87-

2.95 (m, 1H), 2.73 (td, J=5.69, 1.59 Hz, 1H), 2.11 (d, J=9.29 Hz, 1H), 1.57 (s, 3H), 1.00 (s, 3H);

$^{13}$C-NMR (CDCl$_3$, 75 MHz); d203.92, 163.51, 154.33, 149.96, 136.65, 133.90, 131.15, 124.29, 123.13, 58.27, 52.90, 43.86, 39.97, 26.71, 22.12;

HRMS calculated value C$_{16}$H$_{17}$NO (M+H) 240.1388, measured value 240.1392;

HPLC analytical result: (method 1) 98.4% ($t_R$=4.28 min).

Example 1-22: Preparation of (1S,5R)-6,6-dimethyl-4-(E)-2-(pyridin-3-yl)vinyl)bicyclo[3.1.1]hept-3-en-2-one (Compound 5b)

Using a method similar to the preparation method of compound 5a, (1S,5R)-6,6-dimethyl-4-((E)-2-(pyridin-3-yl)vinyl)bicyclo[3.1.1]hept-3-en-2-one (compound 5b) was obtained as a yellow solid showing the following characteristics (yield: 77%). The obtained compound was used as a sample in the Experimental Examples below.

mp 102-104° C.;

$[\alpha]^{20}_D$ –204.0° (c1.0, MeOH); [A] 20 D –204.0° (c 1.0, MeOH);

$^1$H-NMR (CDCl$_3$, 500 MHz); d 8.70 (d, J=1.96 Hz, 1H), 8.54 (dd, J=1.22, 4.65 Hz, 1H), 7.85 (td, J=1.86, 8.01 Hz, 1H), 7.31 (dd, J=4.77, 7.95 Hz, 1H), 7.02 (d, J=16.00 Hz, 1H), 6.91 (d, J=16.00 Hz, 1H), 5.97 (s, 1H), 3.12 (dt, J=1.10, 5.81 Hz, 1H), 2.94 (td, J=5.62, 9.54 Hz, 1H), 2.76 (dt, J=1.71, 5.75 Hz, 1H), 2.13 (d, J=9.54 Hz, 1H), 1.60 (s, 3H), 1.03 (s, 3H);

$^{13}$C-NMR (CDCl$_3$, 75 MHz); d203.72, 163.28, 149.82, 149.35, 133.12, 131.73, 130.98, 129.34, 123.61, 58.23, 52.84, 43.64, 39.96, 26.72, 22.13;

HRMS calculated value C$_{16}$H$_{17}$NO (M+H) 240.1388, measured value 240.1397;

HPLC analytical result: (method 1) 98.7% (t R=3.89 min).

Example 1-23: Preparation of (1S,5R)-6,6-dimethyl-4-(E)-2-(pyridin-4-yl)vinyl)bicyclo[3.1.1]hept-3-en-2-one (Compound 5c)

Using a method similar to the preparation method of compound 5a, (1S,5R)-6,6-dimethyl-4-(E)-2-(pyridin-4-yl)vinyl)bicyclo[3.1.1]hept-3-en-2-one (compound 5c) was obtained as a yellow gel showing the following characteristics (yield: 80%). The obtained compound was used as a sample in the Experimental Examples below.

$[\alpha]^{20}_D$ –152.0° (c1.0, MeOH);

$^1$H-NMR (CDCl$_3$, 500 MHz); d8.62 (d, J=5.87 Hz, 2H), 7.35 (d, J=5.87 Hz, 2H), 7.13 (d, J=16.14 Hz, 1H), 6.84 (d, J=16.14 Hz, 1H), 6.01 (s, 1H), 3.10 (t, J=5.87 Hz, 1H), 2.95 (td, J=5.62, 9.54 Hz, 1H), 2.77 (dt, J=1.59, 5.69 Hz, 1H), 2.13 (d, J=9.54 Hz, 1H), 1.60 (s, 3H), 1.02 (s, 3H);

$^{13}$C-NMR (CDCl$_3$, 75 MHz); d203.57, 162.78, 150.42, 143.12, 131.89, 131.57, 124.62, 121.23, 58.24, 52.90, 43.68, 39.95, 26.70, 22.11;

HRMS calculated value C$_{16}$H$_{17}$NO (M+H) 240.1338, measured value 240.1378;

HPLC analytical result: (method 1) 98.4% ($t_R$=4.29 min).

Example 2: Effects of Verbenone Derivatives on Excitotoxicity, Antioxidant Activity and Focal Cerebral Ischemia Preparation of Experimental Animals SD rats (260-270 g, male) were purchased from Charles River Laboratories (Seoul, Korea) and acclimated to the environment under a 12-hr light/12-hr dark cycle before the experiment. The animals were allowed access to drinking water ad libitum, and the experiment was performed under the approval of the NIH Guide for the Care and Use of Laboratory Animals and the Korea University Institutional Animal Care & Use Committee.

Statistical Analysis

Data were expressed as means±S.E.M., and statistical analysis was performed by one-way analysis of variance (ANOVA) and post-hoc bonferroni test. P<0.05 was considered significant. Before ANOVA analysis, P value of Levene's test for equality of variances was determined (P>0.05). If necessary, the data were further analyzed by Kruskal-Wallis test, followed by Mann-Whitney test.

Example 2-1: The Effect of Verbenone Derivatives on Excitotoxicity

To examine the effects of the samples, obtained in the above Examples, on excitotoxicity, the following experiment was performed according to the method disclosed in the literature (Ju C. et al., BBRC, 431(3), 484-489, 2013).

(1) Culture of Cortical Neurons

Cortical neurons (5×10$^5$ cells/ml) were isolated from fetal SD rats (16-17 days). Specifically, brain cortex was cut, and cells were isolated from the tissue by repeated trituration using a Pasteur pipette in buffer (Hanks' Balanced Salt Solution, HBSS). The cell suspension (1.8×10$^3$ cells/mm$^2$) was dispensed on a plate pretreated with poly-D-lysine (100 mg/ml)/laminin (4 mg/ml). The cells were placed in 10% FBS-containing NBM medium, and incubated in a 96% air/5% CO$_2$ atmosphere at 37° C. After 15-16 days of the incubation, the experiment was performed.

(2) Reoxygenation after OGD (Oxygen-Glucose Deprivation)

In order to induce hypoxic-ischemic symptoms in vitro, the incubated cells were placed in an anoxic chamber (partial oxygen pressure <2 mmHg). The cells were incubated glucose-free DMEM while being bubbled with an anaerobic gas mixture (95% N$_2$ and 5% CO$_2$) for 30 minutes to remove residual oxygen, and were incubated at 37° C. for 90 minutes for oxygen deprivation. After 90 minutes, the exposed solution was replaced with 25 mmol/L glucose-containing DMEM medium to stop the OGD reaction, and the cells were restored to normal oxygen conditions. Control cells not exposed to OGD were incubated in glucose (25 mmol/L)-containing DMEM medium provided with an aerobic gas mixture (95% air and 5% CO$_2$). The cells were treated with each sample 30 minutes before, and during the entire period of OGD/re-oxygenation.

(3) Measurement of NMDA (N-methyl-D-aspartate)-Induced Excitotoxicity

After incubation on the plate for 15-18 days, the cortical neurons were exposed to NMDA (100 mM) in a solution (Mg$^{2+}$-free Earle's balanced salt solution (EBSS); containing 1.8 mM CaCl$_2$ and 10 mM glycine) for 10 minutes. After exposure, the cells were washed with MgSO$_4$-containing EBSS solution, and incubated in 25 mmol/L glucose-containing DMEM medium in a 5% CO$_2$ incubator at 37° C. 30 Minutes before treatment with NMDA, the cells were treated with each sample (10 mM).

(4) Measurement of Cell Injury or Cell Death

In order to measure cell injury or cell death, the amount of LDH released into the medium was measured using a cell viability measurement kit (Sigma-Aldrich, St. Louis, Mo.). Cell viability was expressed as the percentage of LDH relative to the total cellular LDH level measured in sister cultures lysed by freezing-thawing after the experiment.

Figure 2:
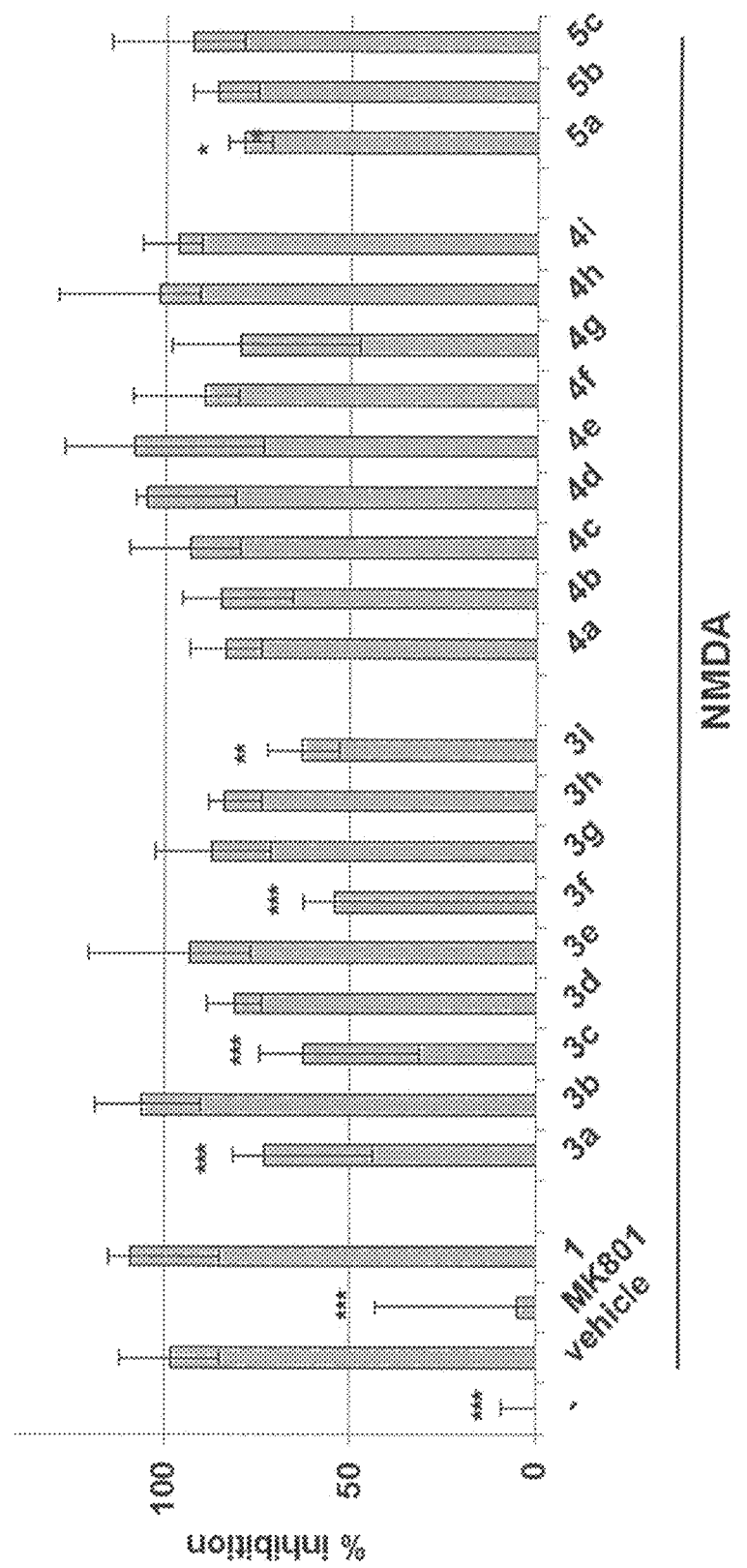
FIG. 2 shows the effects of compound derivatives of the present invention against NMDA-induced excitotoxicity.

Excitotoxicity is a major factor in ischemia-induced neuronal death, particularly early cerebral ischemia. OGD is an experimental model that mimics the abrupt disruption of blood supply and energy consumption in ischemia. Cell injury is induced by OGD and cell membrane injury and neuronal injury can be assessed by measuring the release of a protein such as LDH into media. As a result, it was observed that compounds (3a, 3c and 3f) significantly reduced neuronal injury, comparable to MK801 (already well-known NMDA receptor antagonist), and showed no cytotoxicity (FIG. 1). Excitotoxicity caused by the excessive stimulation of NMDA receptor is a major factor that is involved in neuronal injury during OGD/R and cerebral ischemic injury resulting from the simultaneous generation of free radicals leading to oxidative stress. The results of this experiment indicated that the compounds (3a, 3c, 3f, 3i and 5a) of the present invention significantly reduced NMDA-induced neuronal injury in cultured cortical neuronal cells, even though the activities thereof were lower than the anti-excitotoxic activities of MK-801 (FIG. 2). This suggests that the inhibition of NMDA-induced neuronal excitotoxicity by the compounds of the present invention contribute to anti-ischemic activity.

Example 2-2: Antioxidant Activities of Verbenone Derivatives

In order to examine the direct antioxidant activities of the samples obtained in the Examples above, the following experiment was performed according to the method disclosed in the literature (Ju c. et al., BBRC, 431(3), 484-489, 2013; Huang D. et al., J. Agric. Food Chem., 53, 1841-1856, 2005.)

(1) Measurement of Intracellular Levels (DCF fluorescence) of Reactive Oxygen Species (ROS)

In order to examine the direct radical scavenging activities of the samples, at 1 hour after reoxygenation, the cells were stained with the fluorescent probe H2DCF-DA (2,7-dihydroichlorofluorescein diacetate) that is widely used to measure intracellular oxidative stress. After 2 hours, the cells were washed in EBSS buffer (containing 25 mM glucose, 1.8 mM CaCal$_2$, 1.2 mM MgSO$_4$ and 2.5 mM probenecid (pH7.4)), and the fluorescence of DCF was measured with a fluorescence microplate reader (SpectraMax GeminiEM; Ex=485 nm, Em=530 nm) or a fluorescence microscope (DM IL HC Fluo, Leica, Wetzlar, Germany) equipped with a digital camera (DFC420C, Leica, Wetzlar Germany). The fluorescence intensity was compensated with autofluorescence (i.e., the fluorescence of cells not loaded with H$_2$DCF-DA).

Figure 3:
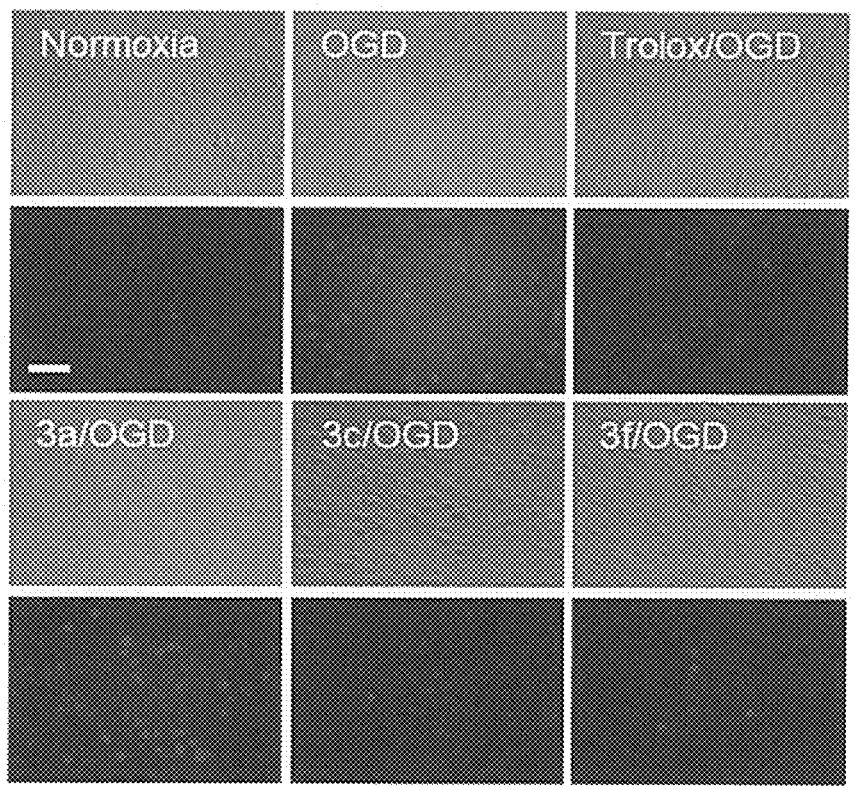
FIG. 3 shows the effects of compound derivatives of the present invention on the inhibition of intracellular oxidative stress.
Figure 3:
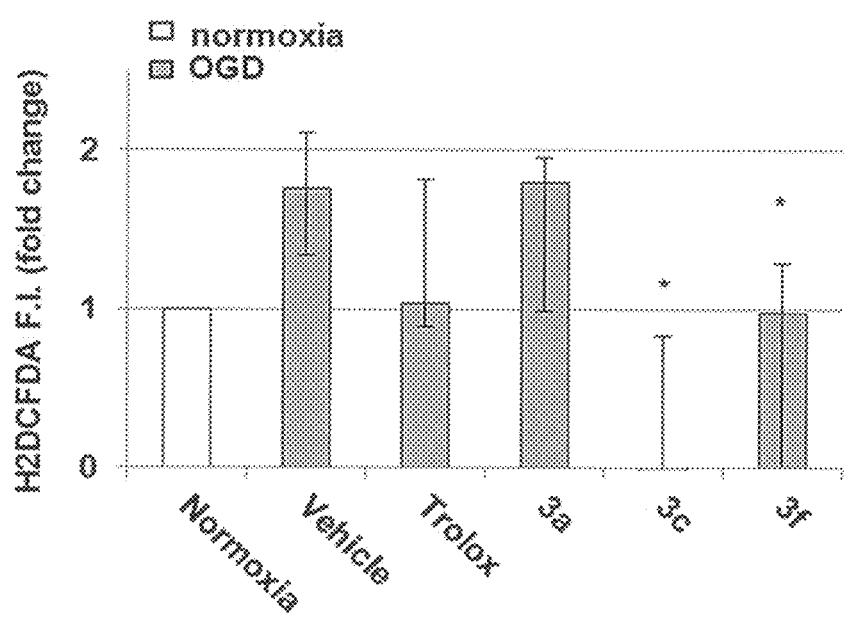

The results of this experiment indicated that compounds 3c and 3f reduced OGD-induced intracellular oxidative stress (FIG. 3).

(2) Measurement of the Ability to Scavenge Nitrogen Radicals (DPPH Assay)

The samples were mixed with DPPH (23.6 μg/ml, in ethanol), and incubated in dark at 37° C. for 30 minutes. The DPPH absorbance reduced by each sample was measured at 517 nm. Vitamin C (Sigma-Aldrich, St. Louis, Mo.) was used as a control, and the DPPH inhibition value (%) was calculated using the following equation:

$$\text{Scavenging activity (\%)} = [\text{Abs}_{max(Vit.C)} - \text{Abs}_{sample}] / [\text{Abs}_{max(Vit.C)} - \text{Abs}_{min(Vit.C)}] \times 100. \quad \text{Equation 1}$$

(3) Measurement of Oxygen Radical Absorbance Capacity (ORAC)

An ORAC assay was performed as disclosed in the literature (Huang, D. et al., J. Agric. Food Chem., 53, 1841-56, 2005).

AAPH (60 mM) and fluorescein (50 nM) were prepared in buffer (75 mM phosphate buffer, pH7.4) without a sample or a sample or a standard (Trolox). Each of the samples and the standard was suspended in a solution of 7% RMCD (randomly methylated beta-cyclodextrin) in 50% acetone. RMCD was used to increase the solubility of oil-soluble samples. Each sample was sufficiently mixed with fluorescein solution (66 nM, 190 μl) by shaking for 5 seconds. After incubation at 37° C. for 10 minutes, AAPH (500 mM, 30 μl) was quickly added to each sample, and a decrease in the fluorescence was measured using a fluorescence microplate reader (Ex=485 nm, Em=530 nm; SpectraMax GeminiEM, Molecular Devices, Sunnyvale, Calif.) at 37° C. at 5-min intervals for 9 hours. To quantify the activity of scavenging peroxyl radicals, AUC (area-under-the-curve) was calculated according to the following equation 2, and net AUC was calculated according to the following equation 3, and the TE (trolox equivalents) of each sample was calculated according to the following equation 4 based on a standard curve of net AUC plotted according to an increase in trolox concentration.

$$AUC=(0.5+f_1/f_0+f_2/f_0+f_3/f_0+\ldots+f_{n-2}/f_0+f_{n-1}/f_0+f_n/f_0)\times 5, \quad \text{Equation 2}$$

peroxyl radical scavenging activities compared to trolox (see Tables 1 and 2). In addition, it was found that the introduction of a hydroxyl group into the meta- and para-positions of the phenyl group increased the free radical scavenging activity of each compound.

TABLE 1

| | Formula 2 | | | | | DPPH assay | ORAC assay | |
|---|---|---|---|---|---|---|---|---|
| | product | | | | | | | |
| code | $R_1$ | $R_2$ | $R_3$ | $R_4$ | $R_5$ | % inhibition[a] | Net AUC[b] | $TE_{25}$[b] |
| 3a | H | H | OH | H | H | 19.11 ± 0.67 | 153.98 ± 1.68 | 3.43 ± 0.04 |
| 3b | $OCH_3$ | H | OH | H | H | 38.13 ± 5.62 | 106.48 ± 1.89 | 2.37 ± 0.04 |
| 3c | H | OH | OH | H | H | 91.62 ± 3.27 | 131.29 ± 11.97 | 3.11 ± 0.11 |
| 3d | H | Br | OH | H | H | 29.45 ± 2.41 | 168.12 ± 5.24 | 3.74 ± 0.12 |
| 3e | $OCH_3$ | H | OH | H | $OCH_3$ | 55.80 ± 7.52 | 166.26 ± 6.05 | 3.70 ± 0.13 |
| 3f | H | OH | OH | $OCH_3$ | H | 83.64 ± 6.19 | 99.06 ± 37.80 | 2.83 ± 0.22 |
| 3g | H | OH | H | H | H | ND | 73.74 ± 3.86 | 1.64 ± 0.09 |
| 3h | OH | H | H | H | H | 4.64 ± 0.60 | 98.77 ± 2.53 | 2.20 ± 0.06 |
| 3i | OH | H | $OCH_3$ | H | H | 51.21 ± 3.83 | 136.87 ± 3.24 | 3.05 ± 0.07 |
| 4a | H | H | H | H | H | ND | 27.73 ± 0.74 | 0.61 ± 0.01 |
| 4b | H | H | F | H | H | ND | 26.15 ± 1.26 | 0.62 ± 0.02 |
| 4c | H | H | $OCH_3$ | H | H | ND | 38.06 ± 2.00 | 0.79 ± 0.01 |
| 4d | H | H | Ph | H | H | ND | 26.75 ± 1.27 | 0.56 ± 0.01 |
| 4e | H | H | Pyrrol | H | H | ND | 98.31 ± 0.48 | 2.19 ± 0.01 |
| 4f | H | $OCH_3$ | $OCH_3$ | H | H | ND | 39.35 ± 1.67 | 0.88 ± 0.04 |
| 4g | H | $OCH_3$ | H | $OCH_3$ | H | ND | 45.28 ± 0.62 | 1.01 ± 0.01 |
| 4h | $OCH_3$ | H | H | $OCH_3$ | H | ND | 32.44 ± 1.54 | 0.72 ± 0.03 |
| 4i | $OCH_3$ | H | H | Br | H | ND | 32.96 ± 1.03 | 0.73 ± 0.02 |

Formula 2

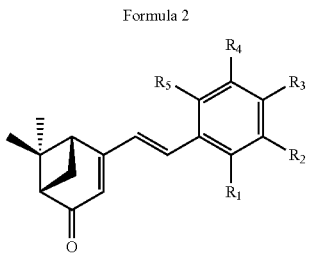

wherein $f_0$ is the first fluorescence at 0 min and time I.

$$\text{Net AUC} = AUC_{sample} - AUC_{blank}. \quad \text{Equation 3}$$

TE(trolox equivalents) of each sample=
[netAUC$_{sample}$ at 25 mM]/[net AUC$_{trolox}$ at 25 mM]. Equation 4

The antioxidant activities of the verbenone derivatives of the present invention were measured by the following two different chemical reactions: (1) a single electron transfer-based assay that is a 2,2-di(4-tert-octylphenyl)-1-picrylhydrazyl [DPPH] assay that measures a decrease in DPPH acting as a free radical generator and a termination probe; and (2) a hydrogen atom transfer assay that is an oxygen radical absorbance capacity [ORAL] assay that measures the competitive reaction kinetics of a peroxyl radical generator (AAPH; 2,2'-azobis-(2-methylpropionamide)-dihydrochloride) and each sample acting as an antioxidant for oxidizable fluorescent probe (fluorescein).

The results of this experiment indicated that, in the DPPH assay, most of the styryl derivatives (3a-f, and 3h-i) having a phenol group showed a strong and direct scavenging activity against the conversation of DPPH to organic nitrogen free radicals (see Table 1). Among them, compounds 3c and 3f showed a stronger scavenging activity compared to vitamin C at the same concentration. In the ORAC assay, it was shown that compound (4e) having a pyrrole group and compounds (3a-i) having a phenol group all showed strong

TABLE 2

| | Formula 3 | | | DPPH assay | ORAC assay | |
|---|---|---|---|---|---|---|
| | product | | | | | |
| code | X | Y | Z | % inhibition[a] | Net AUC[b] | $TE_{25}$[b] |
| 5a | N | C | C | ND | 23.51 ± 0.79 | 0.52 ± 0.02 |
| 5b | C | N | C | ND | 22.93 ± 0.61 | 0.51 ± 0.01 |
| 5c | C | C | N | ND | 22.51 ± 0.34 | 0.50 ± 0.01 |

Formula 3

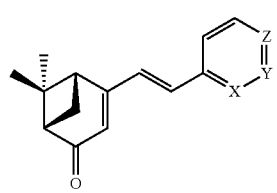

Example 2-3: Experiment in Focal Cerebral Ischemia Model

In order to examine the effects of the samples, obtained in the Examples above, on focal cerebral ischemia, the following experiment was performed according to the method disclosed in the literature (Belayev L. et al., Stroke, 27, 1616-1622, 1996; discussion 1623).

(1) Focal Cerebral Ischemia Model

Rats were anesthetized with 3.0% isoflurane in $N_2O$ and $O_2$ (70:30 v/v) mixture via facemask and were maintained in 2% isoflurane. Throughout the experimental period, the body temperature was controlled and kept to 37° C.±0.3° C. using a rectal thermometer and a heating pad until the animals were sufficiently recovered from anesthesia after surgery. Focal cerebral ischemia was achieved by right-sided endovascular MCAO. Briefly, a 3-0 heat-blunted monofilament nylon suture (Ethicon Johnson & Johnson, Brussels, Belgium) were inserted into the lumen of the right external carotid artery stump and advanced 17.5 mm into the internal carotid artery to occlude the ostium of the MCA. The suture was removed after 1.5 hours to allow animals to recover. Operated controls were subjected to the same surgical procedures, except for MCAO. Physiological values were measured 15 minutes before MCAO and at 15 minutes after reperfusion, and mean blood pressure was monitored for 5 minutes using a blood pressure analyzer (MicroMed, Lousville, Ky.), and glucose were monitored using an analyzer (Ciba Corning Diagnostics Corp., Medfield, Mass.). A 5% sample (compound 30 was dissolved in DMSO, diluted with 10% cremophore and sterile saline, and was intraperitoneally administrated to rats from 2 hours after MCAO induction (100 mg/kg).

(2) Measurement of Infarct Volume

Rats were anesthetized with 3.5% chloral hydrate (5 ml/kg, intraperitoneal injection) and decapitated. Coronal sections of brain (2 mm) obtained using a matrix (rat brain matrix, Ted Pella, Redding, Calif.) were stained with 2% triphenyltetrazolium chloride (Sigma-Aldrich, St. Louis, Mo.) at 37° C. for 30 minutes, fixed with 4% paraformaldehyde (pH 7.4), and subsequently cryoprotected in phosphate buffer containing 30% sucrose at 4° C. for 2 days. The cross-sectional area of infarction between the bregma levels of +4 mm (anterior) and −6 mm (posterior) were determined with analysis software (OPTIMAS5.1 image analysis program, BioScanInc. Edmonds, Wash.). Brain infarct size was measured manually by outlining the margins of infarct areas. The total infarction volume ($mm^3$) was calculated according to the following equation 5 as disclosed in a document (J Neurosci Methods (1998) 84:9-16; J Cereb Blood Flow Metab (1990) 10:290-293), and compensated for brain edema. Cerebral edema was determined by the percent increase of the ipsilateral/contralateral hemisphere area as shown in the following equation 6. The measurements were all done in a double-blind manner.

Total infraction volume ($mm^3$)=ipsilateral volume ($IVd$) obtained by direct measurement×[(contralateral volume ($Vc$))/ipsilateral volume ($V_I$)]  Equation 5

Edema volume) (%)=[(ipsilateral volume ($V_I$)−contralateral volume ($Vc$))/contralateral volume ($Vc$)]×100.  Equation 6

Thereafter, the tissues were frozen, cut into 10- or 30-μm coronal sections and stored at −20° C.

(3) Measurement of Neurological Loss

Neurological loss was measured at 24 hours after ischemia, and rated on a 4-point scale as disclosed in the literature (0: no neurological loss, 1: paw was bent, 2: bent paw, reduced resistance to the force that pushes the side, and not rotated; 3: the same as 2, but rotated).

(4) Immunohistological Staining of Brain Tissue

The brain tissue sections prepared as described above were treated with 5% serum-containing buffer at room temperature for 1 hour in order to inhibit non-specific antibody binding. Primary antibodies diluted to suitable concentrations (MPO antibody and ED-1-antibody, each 1:100; Nitrotyrosine antibody, 1:50; IL-1a, IL-1b, TNF-a antibodies, each 1:100) were added to the tissue sections which were then stained overnight at 4° C. Non-bound primary antibody was removed by washing, and then the tissue sections were stained with fluorescence-labeled secondary antibodies at room temperature for 1 hour. Non-bound secondary antibody was removed by washing, and then the nucleus was stained with Hoechst 33258 dye for 20 minutes, followed by washing. The sections were mounted on a glass slide, and then observed with a confocal fluorescence microscope (Zeiss LSM510; Zeiss, Oberkochen, Germany).

(5) Experiment on Blood-Brain Barrier Permeability

Staining dye (Evans blue dye, 2%) binds to serum albumin immediately after intravenous injection and is converted to a high molecular weight material incapable of passing through a normal blood-brain barrier, but in brain ischemia-induced rat brain tissue, the permeability of Evans blue is increased because of damage to the blood-brain barrier, and thus the amount of staining with Evans blue increases. The heart of the rats having focal cerebral ischemia induced as described above was perfused with 200 ml of physiological saline. The brain tissue was extracted, weighed, and maintained in a reagent (trichloroacetic acid, 60%) at 4° C. for 24 hours. The tissue was ground, and centrifuged at 10,000 rpm for 15 minutes, and the supernatant was collected. The absorbance of Evans blue in the brain tissue was measured at 610 nm and calculated as the amount of dye per gram of tissue.

(6) Experiment on Long-Term Survival Rate

For rats having focal cerebral ischemia induced as described above, survival rate and neurological deficit were measured over 3 weeks under the same conditions as those before surgery.

(7) Embolic Ischemic Stroke Animal Model

Rats (weight: 270-300 g) were anesthetized with 3.0% isoflurane in a 70% $N_2O$/30% $O_2$ (70:30 v/v) mixture and were maintained in 3% isoflurane. A rectal thermometer was inserted into the rats, and the body temperature of the rats was maintained at 37.0-37.9° C. using an automatic heating pad connected to the thermometer. The midline of the neck was incised, the right common carotid artery (CCA), the right external carotid artery (ECA) and the right internal carotid artery (ICA) were separated, and the external carotid artery and the common carotid artery were tied. The internal carotid artery was temporarily tightened using a bent microvascular clip. The branches starting from the external carotid artery and the internal carotid artery were incised, and 35 mm embolus was injected into the internal carotid artery by a 100 ul Hamilton syringe using a modified PE-50 catheter (outer diameter: 0.58 mm; inlet diameter: 0.3 mm suitable for intravascular injection). The microvascular clip was removed, and the catheter was carefully advanced 16-17 mm into the internal carotid artery and moved to a point corresponding to about 2 mm from the start point of the middle cerebral artery. The embolus of the catheter was injected into the internal carotid artery (10 ul). At 5 minutes after embolus injection, the catheter was removed. The internal carotid artery branch was tied, and the incision site was sutured, and then rats were allowed to stand until recovery from anesthesia. Embolus to be used in the experiment was obtained by injecting femoral arterial blood (collected from donor rats) quickly into a PE-50 tube and allowing the blood to stand at room temperature for 2 hours and at 4° C. for 22 hours to produce thrombi. Before the experiment, the tube was cut, and the thrombi were transferred to a modified PE-50 catheter through a PE-10 tube using a saline-containing 1 ml syringe equipped with a 23 G needle.

Figure 4:
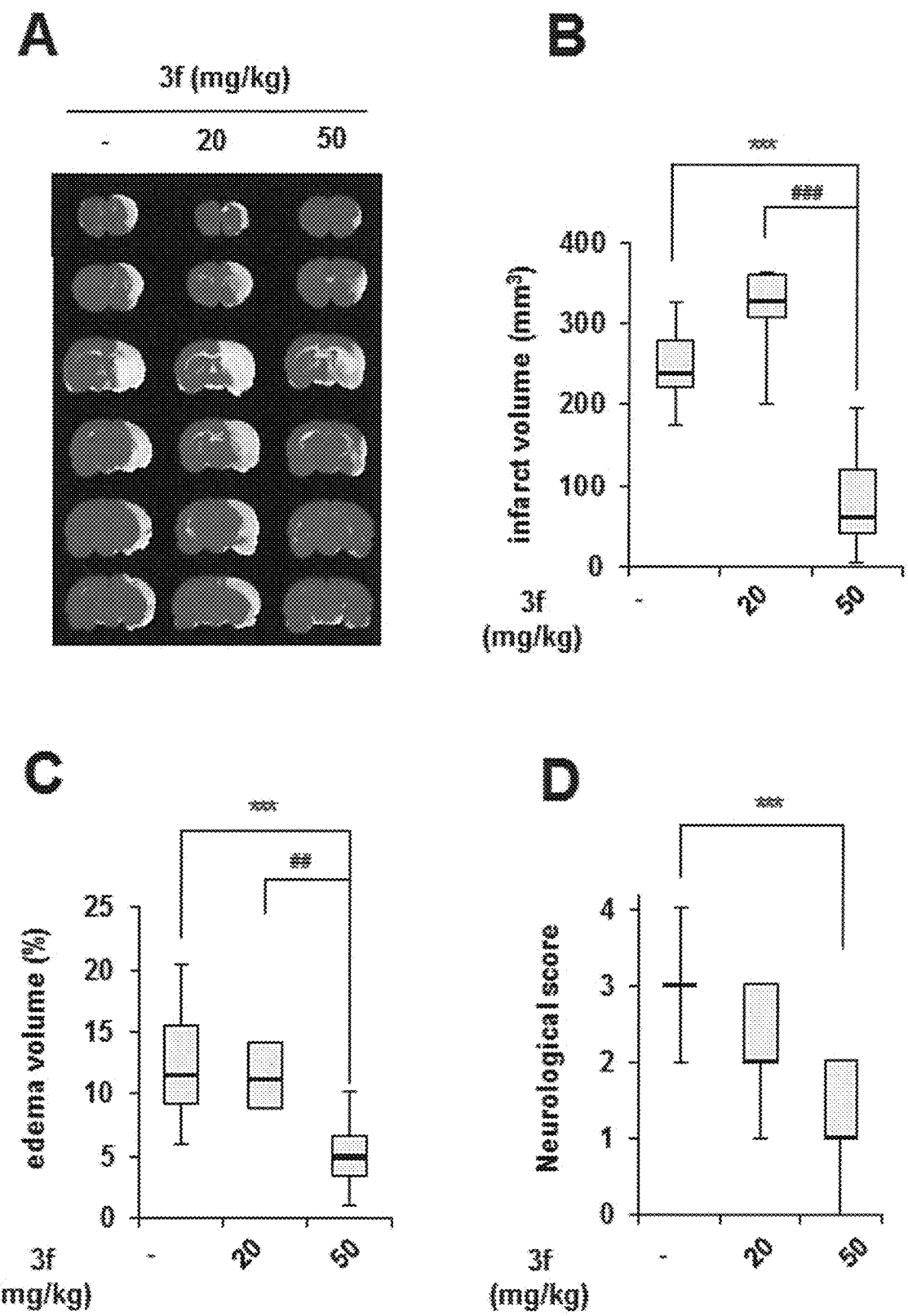
FIG. 4 shows the effects of compound derivatives of the present invention on the reduction of ischemic injury, brain edema and neurological deficits in an in vivo focal cerebral ischemia model.
Figure 5:
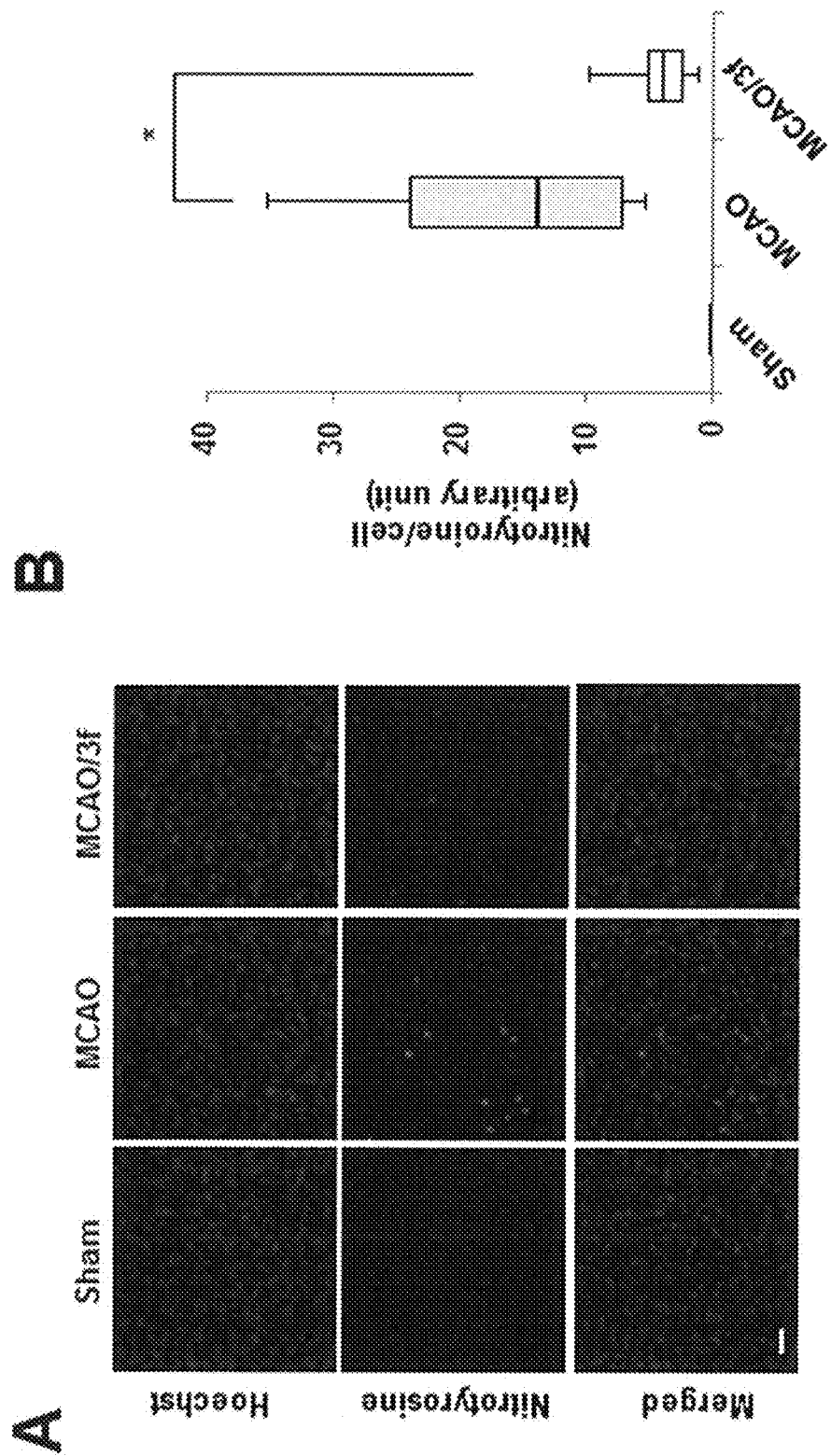
FIG. 5 shows the effects of compound derivatives of the present invention on an increase in antioxidant activity in ischemic injured brain tissue in an in vivo focal cerebral ischemia model.

The results of the experiment indicated that, in the transient ischemia-induced rat model, post-ischemic treatment with sample 3f (50 mg/kg) (intraperitoneal injection; administered twice (i.e., 2 hours and 7 hours after brain infarction)) significantly reduced ischemic injury, cerebral edema and neurological deficit (FIG. 4). In addition, when antioxidant activity in tissue was measured by immunohistological staining for nitrotyrosine in the brain tissue sections obtained from the rats administered with the samples, it was shown that the antioxidant activity in the brain tissue of the sample-treated group was significantly increased (FIG. 5).

Figure 6:
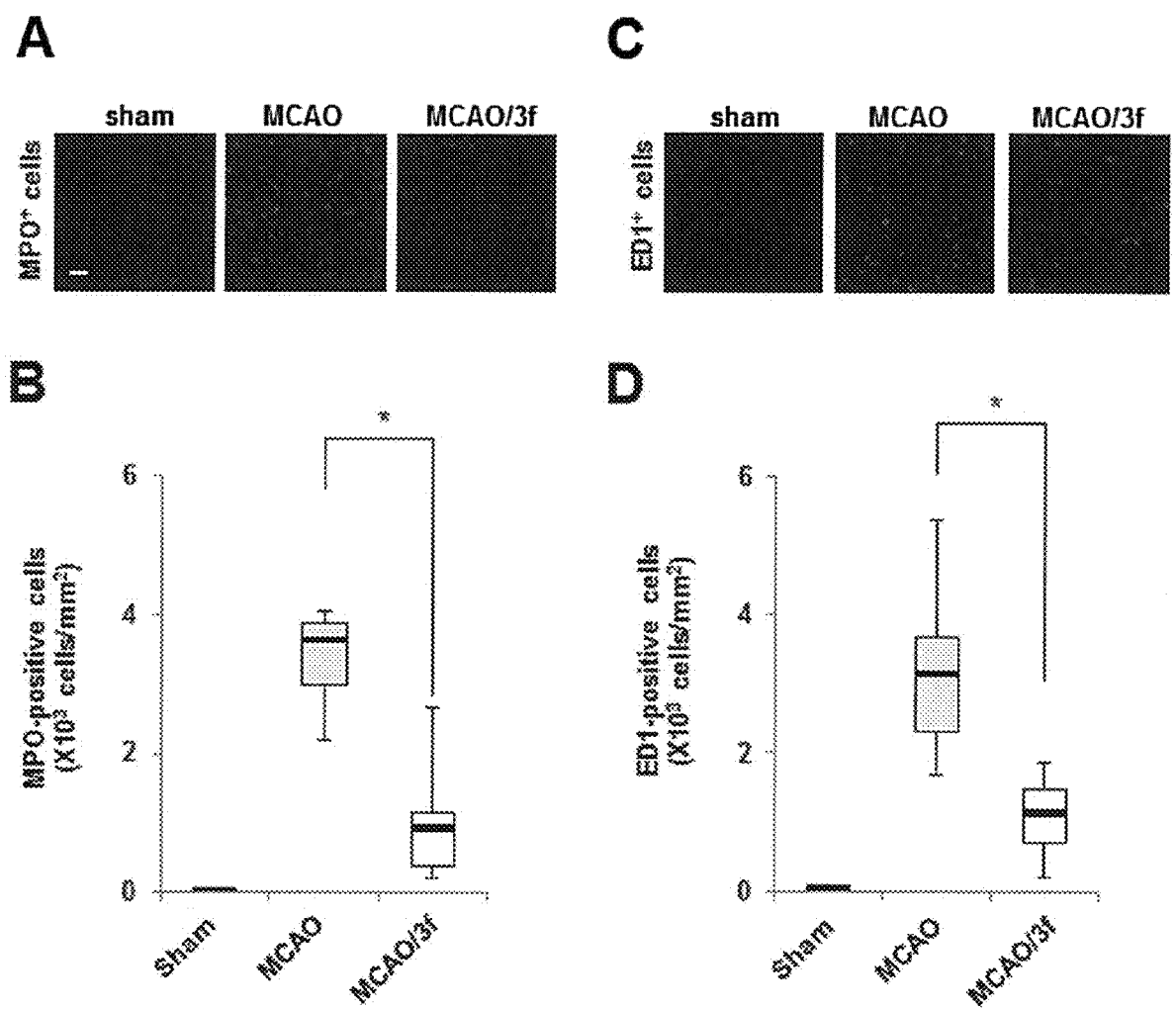
FIG. 6 shows the effects of compound derivatives of the present invention on the inhibition of the migration and infiltration of inflammatory cells into ischemic injured brain tissue in an in vivo focal cerebral ischemia model.
Figure 7:
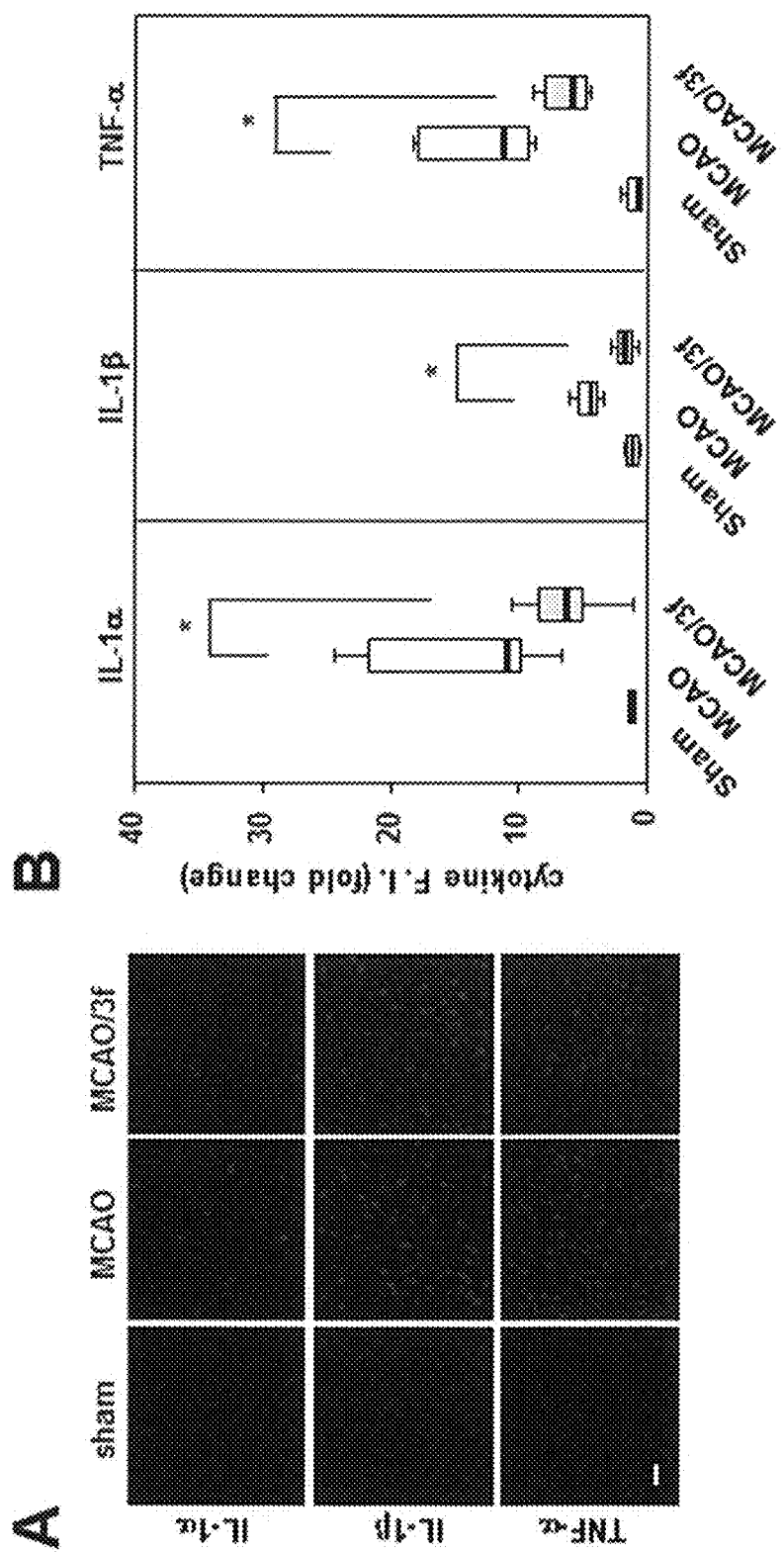
FIG. 7 shows the effects of compound derivatives of the present invention on the inhibition of cytokine expression in ischemic injured brain tissue in an in vivo focal cerebral ischemia model.
Figure 8:
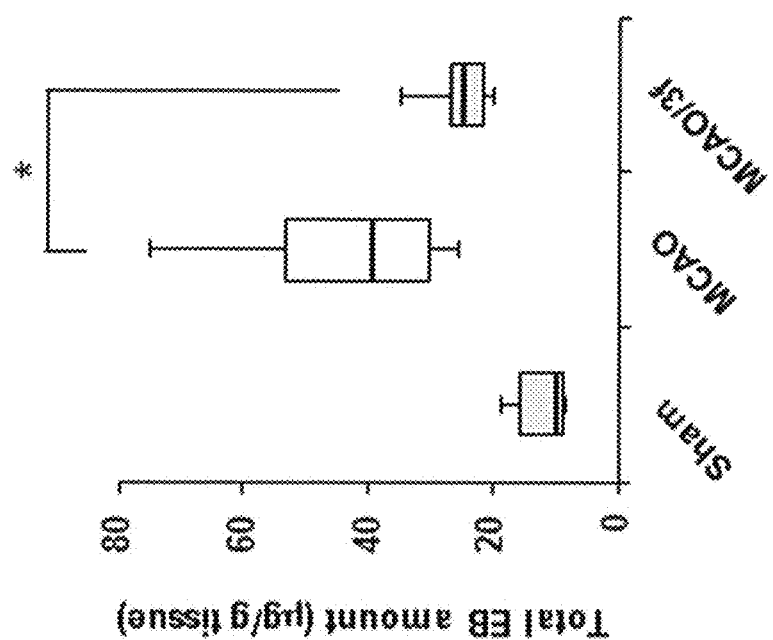
FIG. 8 shows the effects of compound derivatives of the present invention on the inhibition of an increase in blood-brain barrier permeability around ischemic injured brain tissue in an in vivo focal cerebral ischemia model.
Figure 8:
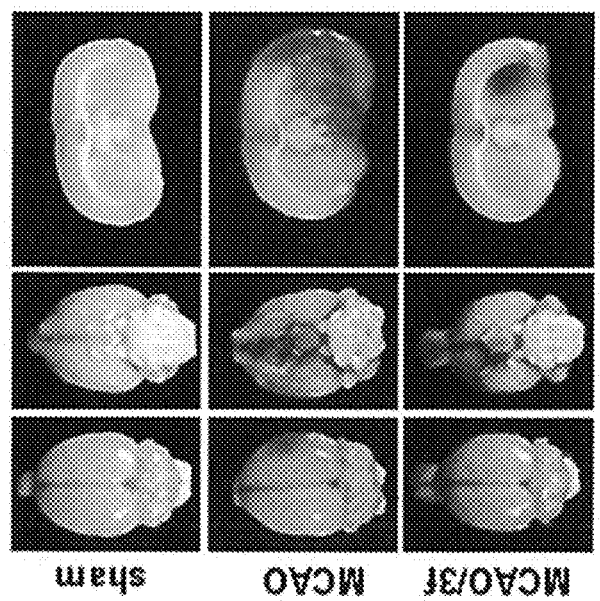
Figure 9:
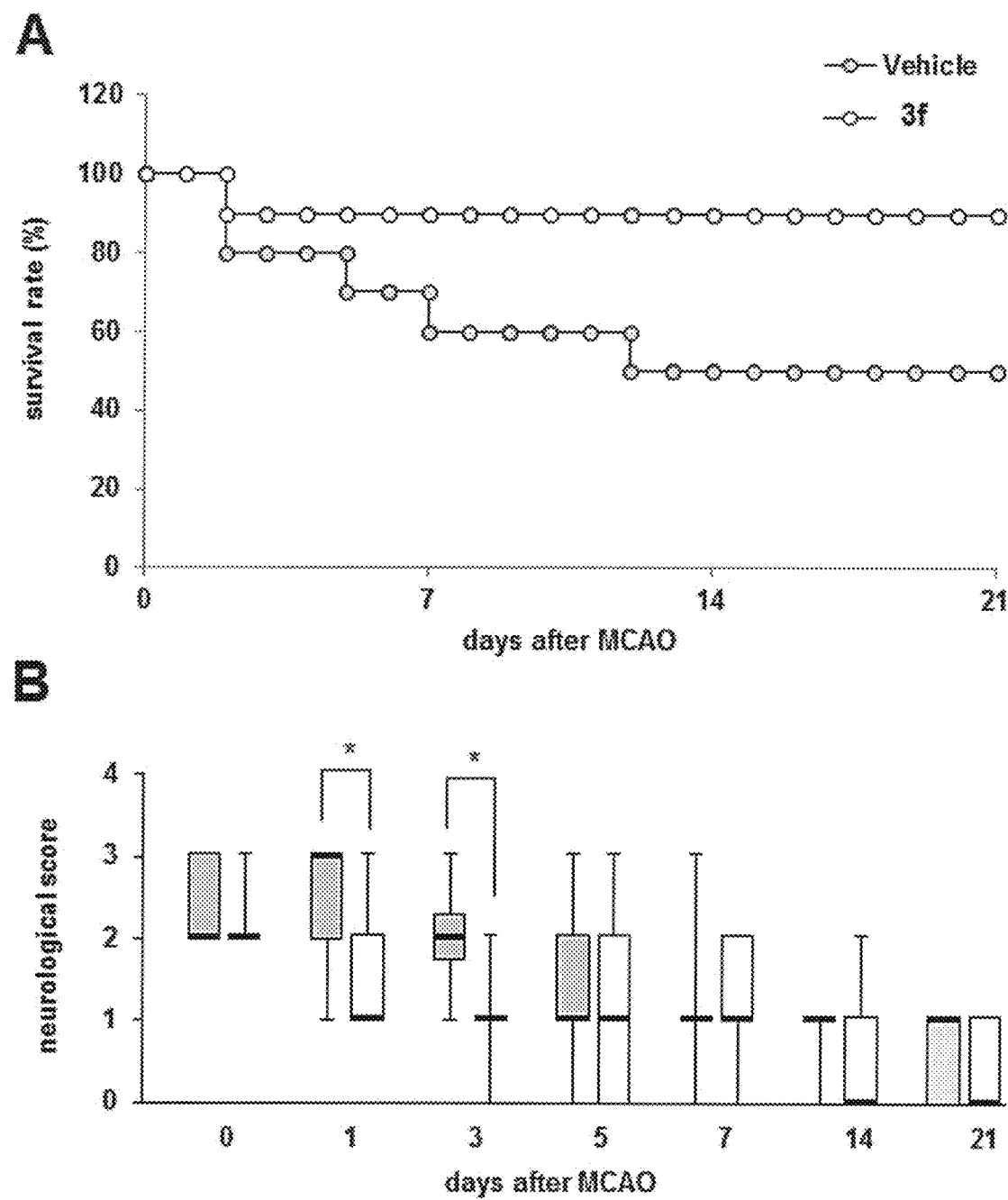
FIG. 9 shows the effects of compound derivatives of the present invention on increases in the long-term survival rate and neurological recovery of rats having ischemic injury in in vivo focal cerebral ischemia models.
Figure 10:
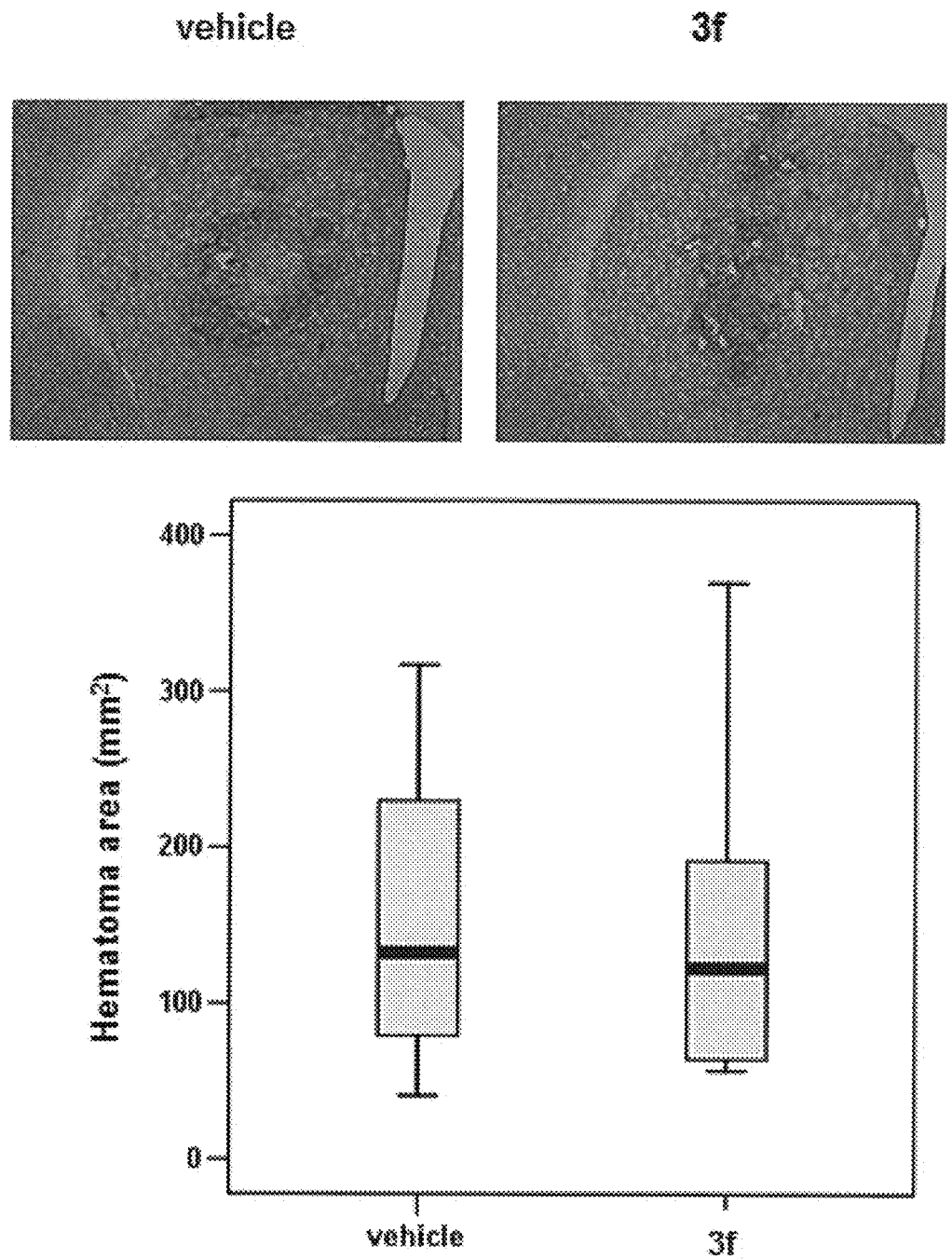
FIG. 10 shows that compound derivatives of the present invention do not show a significant increase in the area of autologous blood-induced hematoma in an in vivo hemorrhagic stroke model.

Meanwhile, when the infiltration of inflammatory cells into brain infarction areas and injured brain areas was examined by immunological staining, it was observed that the migration of neutrophils/monocytes stained with MPO antibody and microglia/macrophages stained with ED-1 antibody was significantly inhibited (FIG. 6). In addition, it was found that the expression levels of cytokines (such as IL-1 alpha, IL-1 beta, and TNF-alpha, known to play an important role in ischemic injury) in tissue were significantly decreased in the group administered with the samples (FIG. 7). Moreover, it was found that the compounds of the present invention significantly reduced the blood-brain barrier permeability that was increased by ischemic injury (FIG. 8). Also, when the effects of the samples (compounds) of the present invention on long-term survival rate and neurological recovery were observed over 3 weeks after administration of the samples to the temporal ischemia-induced rat models, it was found that the long-term survival rate and neurological recovery of the rats administered with the samples were significantly increased (FIG. 9). In the case of ischemic stroke, the increase in bleeding by a drug (e.g., tPA) frequently occur, which can increase clinical side effects (e.g., death or bad prognosis) in the patients. However, the samples of the present invention did not significantly influence the size of brain injury in the in vivo animal models having embolic stroke induced by autologous blood, suggesting that there is low possibility that the samples of the present invention cause such side effects (FIG. 10).

Hereinafter, formulation examples of a compound containing the compound of the present invention will be described, but these formulation examples are for illustrative purposes only and are not intended to limit the scope of the present invention.

Formulation Example 1: Preparation of Powder

| | |
|---|---|
| Compound 3f | 200 mg |
| Lactose | 100 mg |
| Talc | 10 mg |

The above compounds are mixed with one another and filled into an airtight sachet to prepare a powder formulation.

Formulation Example 2: Preparation of Tablet

| | |
|---|---|
| Compound 3c | 200 mg |
| Corn starch | 100 mg |
| Lactose | 100 mg |
| Magnesium stearate | 2 mg |

The above components are mixed with one another, and then compressed into a tablet according to a conventional method, thereby preparing a tablet formulation.

Formulation Example 3: Preparation of Capsule

| | |
|---|---|
| RW | 200 mg |
| Crystalline cellulose | 3 mg |
| Lactose | 14.8 mg |
| Magnesium stearate | 0.2 mg |

According to a conventional capsule preparation method, the above components were mixed with each other and filled in a gelatin capsule, thereby preparing a capsule formulation.

Formulation Example 4: Preparation of Injectable Solution

| | |
|---|---|
| Compound 4e | 200 mg |
| Mannitol | 180 mg |
| Injectable sterile distilled water | 2974 mg |
| $Na_2HPO_4, 12H_2O$ | 26 mg |

According to a conventional injectable solution preparation method, a mixture of the above components is filled into each ampoule (2 ml).

Formulation Example 5: Preparation of Liquid Formulation

| | |
|---|---|
| Compound 5a | 200 mg |
| Isomerized sugar | 10 g |
| Mannitol | 5 g |
| Purified water | q.s. |

According to a conventional method for preparing a liquid formulation, each of the above components was dissolved in purified water, and lemon fragrance is added thereto. Then, purified water is added to the mixture to a total volume of 100 ml, and the solution was filled into a brown bottle and sterilized, thereby preparing a liquid formulation.

Formulation Example 6: Preparation of Health Functional Food

| | |
|---|---|
| Compound 3a | 1000 mg |
| Vitamin mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium phantotenate | 0.5 mg |
| Mineral mixture | q.s. |
| Ferrous sulfate | 1.75 mg |
| Zinc oxide | 0.82 mg |
| Magnesium carbonate | 25.3 mg |

-continued

| | |
|---|---|
| Potassium phosphate monobasic | 15 mg |
| Calcium phosphate dibasic | 55 mg |
| Potassium citrate | 90 mg |
| Calcium carbonate | 100 mg |
| Magnesium chloride | 24.8 mg |

The contents of components in each of the vitamin and mineral mixtures are relatively suitable contents for health functional foods, but may be modified to any other values. According to a conventional method for preparing health functional foods, the above components are mixed with one another, and then granulated, and the granules may be used in the preparation of health functional foods according to a conventional method.

Formulation Example 7: Preparation of Health Functional Beverage

| | |
|---|---|
| Compound 3f | 1000 mg |
| Citric acid | 1000 mg |
| Oligosaccharide | 100 g |
| Plum concentrate | 2 g |
| Taurine | 1 g |
| Purified water | To 900 ml |

According to a conventional method for preparing health functional beverages, the above components are mixed with one another, and then stirred and heated at 85° C. for about 1 hour. Then, the solution is filtered, filled into a 2l sterilized container, sealed, cold-stored, and then used in the preparation of the health functional beverage of the present invention.

The above-described composition ratio is relatively suitable for favorite beverages, but may vary according to locational and ethnic preferences such as consumer hierachy, consumer countries, the intended use, and the like.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

As described above, the pharmaceutical composition containing a verbenone derivative as an active ingredient shows effects on the protection of neurons, the inhibition of NMDA-induced excitotoxicity, the inhibition of intracellular oxidative stress, and the inhibition of migration of inflammatory cells, compared to conventional pharmaceutical compositions. Thus, it has the effects of treating degenerative brain diseases, specifically cerebral ischemic injury. In addition, it may also be used in health functional foods.

What is claimed is:

1. A verbenone derivative represented by a following Formula 1 or a pharmaceutically acceptable salt thereof:

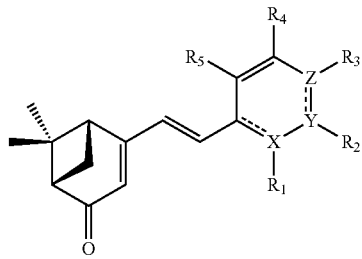

Formula 1 wherein $R_1$, $R_2$, $R_3$, $R_4$ and $R_5$ are each independently a hydrogen atom, a halogen atom, a hydroxyl group, a $C_1$-$C_3$ alkyl group, a $C_1$-$C_3$ alkoxy group, an amino group, a $C_1$-$C_3$ alkylamine group, a $C_1$-$C_3$ alkyldiamine group, a $C_5$-$C_8$ aromatic ring, a $C_5$-$C_8$ cyclic ring, or a $C_5$-$C_8$ heteroaromatic ring;

X, Y and Z are each independently a carbon atom, N atom, O atom or S atom; and $\rule{1cm}{0.4pt}$ denotes a double bond or a single bond.

2. The verbenone derivative of claim 1, wherein $R_1$, $R_2$, $R_3$, $R_4$ and $R_5$ are each independently a hydrogen atom, a halogen atom, a hydroxyl group, a methyl group, an ethyl group, a methoxy group, an ethoxy group, an amino group, a $C_5$-$C_6$ aromatic ring, a $C_5$-$C_6$ cyclic ring, or a $C_5$-$C_6$ heteroaromatic ring.

3. The verbenone derivative of claim 2, wherein $R_1$, $R_2$, $R_3$, $R_4$ and $R_5$ are each independently a hydrogen atom, a halogen atom, a hydroxyl group, a methyl group, a methoxy group, a phenyl group, a pyrrole group, or a pyridine group.

4. The verbenone derivative of claim 1, wherein the X, Y and Z are each independently a carbon atom or N atom, O atom or S atom.

5. The verbenone derivative of claim 4, wherein the X, Y and Z are each independently a carbon atom or an N atom.

6. The verbenone derivative of claim 1, which is:
(1S,5R)-4-(4-hydroxystyryl)-6,6-dimethylbicyclo[3.1.1]hept-3-en-2-one (3a);
(1S,5R)-4-(4-hydroxy-2-methoxystyryl)-6,6-dimethylbicyclo[3.1.1]hept-3-en-2-one (3b);
(1S,5R)-4-(3,4-dihydroxystyryl)-6,6-dimethylbicyclo[3.1.1]hept-3-en-2-one (3c);
(1S,5R)-4-(3-bromo-4-hydroxystyryl)-6,6-dimethylbicyclo[3.1.1]hept-3-en-2-one (3d);
(1S,5R)-4-(4-hydroxy-2,6-dimethoxystyryl)-6,6-dimethylbicyclo[3.1.1]hept-3-en-2-one (3e);
(1S,5R)-4-(3,4-dihydroxy-5-methoxystyryl)-6,6-dimethylbicyclo[3.1.1]hept-3-en-2-one (3f);
(1S,5R)-4-(3-hydroxystyryl)-6,6-dimethylbicyclo[3.1.1]hept-3-en-2-one (3g);
(1S,5R)-4-(2-hydroxystyryl)-6,6-dimethylbicyclo[3.1.1]hept-3-en-2-one (3h);
(1S,5R)-4-(2-hydroxy-4-methoxystyryl)-6,6-dimethylbicyclo[3.1.1]hept-3-en-2-one (3i);
(1S,5R)-6,6-dimethyl-4-styryl-bicyclo[3.1.1]hept-3-en-2-one (4a);
(1S,5R)-4-(4-fluorostyryl)-6,6-dimethylbicyclo[3.1.1]hept-3-en-2-one (4b);
(1S,5R)-4-(4-methoxystyryl)-6,6-dimethylbicyclo[3.1.1]hept-3-en-2-one (4c);
(1S,5R)-4-(2-(biphenyl-4-yl)vinyl)-6,6-dimethylbicyclo[3.1.1]hept-3-en-2-one (4d);
(1S,5R)-4-(4-(1H-pyrrol-1-yl)styryl)-6,6-dimethylbicyclo[3.1.1]hept-3-en-2-one (4e);

(1S,5R)-4-(3,4-dimethoxystyryl)-6,6-dimethylbicyclo[3.1.1]hept-3-en-2-one (4f);
(1S,5R)-4-(3,5-dimethoxystyryl)-6,6-dimethylbicyclo[3.1.1]hept-3-en-2-one (4g);
(1S,5R)-4-(2,5-dimethoxystyryl)-6,6-dimethylbicyclo[3.1.1]hept-3-en-2-one (4h);
(1S,5R)-4-(5-bromo-2-methoxystyryl)-6,6-dimethylbicyclo[3.1.1]hept-3-en-2-one (4i);
(1S,5R)-6,6-dimethyl-4-((E)-2-(pyridin-2-yl)vinyl)-bicyclo[3.1.1]hept-3-en-2-one (5a);
(1S,5R)-6,6-dimethyl-4-((E)-2-(pyridin-3-yl)vinyl)-bicyclo[3.1.1]hept-3-en-2-one (5b); or
(1S,5R)-6,6-dimethyl-4-((E)-2-(pyridin-4-yl)-vinyl)-bicyclo[3.1.1]hept-3-en-2-one (5c).

7. The verbenone derivative of claim 1, which is:
(1S,5R)-4-(4-hydroxystyryl)-6,6-dimethylbicyclo[3.1.1]hept-3-en-2-one (3a);
(1S,5R)-4-(3,4-dihydroxystyryl)-6,6-dimethylbicyclo[3.1.1]hept-3-en-2-one (3c);
(1S,5R)-4-(3,4-dihydroxy-5-methoxystyryl)-6,6-dimethylbicyclo[3.1.1]hept-3-en-2-one (3f);
(1S,5R)-4-(2-hydroxy-4-methoxystyryl)-6,6-dimethylbicyclo[3.1.1]hept-3-en-2-one (3i);
(1S,5R)-6,6-dimethyl-4-((E)-2-(pyridin-2-yl)vinyl)-bicyclo[3.1.1]hept-3-en-2-one (5a);
or a pharmaceutically acceptable salt thereof.

8. The verbenone derivative of claim 1, which is (1S,5R)-4-(3,4-dihydroxy-5-methoxystyryl)-6,6-dimethylbicyclo[3.1.1]hept-3-en-2-one (3f).

* * * * *

UNITED STATES PATENT AND TRADEMARK OFFICE
CERTIFICATE OF CORRECTION

| | | |
|---|---|---|
| PATENT NO. | : 10,710,951 B2 | Page 1 of 1 |
| APPLICATION NO. | : 15/432522 | |
| DATED | : July 14, 2020 | |
| INVENTOR(S) | : Won Ki Kim et al. | |

It is certified that error appears in the above-identified patent and that said Letters Patent is hereby corrected as shown below:

On the Title Page

Page 2, Item (56), OTHER PUBLICATIONS, right-hand column, Line 58: "Margall" should be -- Margaill --.

In the Specification

Column 1, Line 50: "transmit&" should be -- transmit --.

Column 3, Line 43: "170-estradiol" should be -- 17β-estradiol --.

Column 3, Line 45: "170-estradiol" should be -- 17β-estradiol --.

Signed and Sealed this
Eighteenth Day of August, 2020

Andrei Iancu
*Director of the United States Patent and Trademark Office*